(12) United States Patent
Lang et al.

(10) Patent No.: US 6,994,990 B1
(45) Date of Patent: Feb. 7, 2006

(54) ACTIVE MODIFIED HEDGEHOG PROTEINS

(75) Inventors: Kurt Lang, Penzberg (DE); Ulrike Leser, München (DE); Tilman Seytter, Lochham (DE)

(73) Assignee: Curis, Inc., Cambridge, MA (US)

( * ) Notice: Subject to any disclaimer, the term of this patent is extended or adjusted under 35 U.S.C. 154(b) by 362 days.

(21) Appl. No.: 09/198,975

(22) Filed: Nov. 24, 1998

(30) Foreign Application Priority Data

Nov. 28, 1997 (EP) .............................................. 97120891
Feb. 6, 1998 (EP) ............................................ 98102095

(51) Int. Cl.
*C12P 21/06* (2006.01)

(52) U.S. Cl. .................. 435/69.1; 435/69.5; 435/252.3; 435/320.1; 514/2; 530/351

(58) Field of Classification Search .................. 530/351; 435/320.1, 252.3, 69.1, 69.5; 514/2

See application file for complete search history.

(56) References Cited

U.S. PATENT DOCUMENTS

| 5,364,839 A | 11/1994 | Gerhart et al. | |
| 5,844,079 A | * 12/1998 | Ingham et al. .............. | 530/350 |
| 6,444,793 B1 | * 9/2002 | Pepinsky | |

FOREIGN PATENT DOCUMENTS

| WO | WO 93/00050 | 1/1993 |
| WO | WO 95/16035 | 6/1995 |
| WO | WO 96/16668 | 6/1996 |
| WO | WO 97/35607 | 10/1997 |
| WO | WO 98/02454 | 1/1998 |
| WO | WO 98/30576 | 7/1998 |

OTHER PUBLICATIONS

Cha et al., PNAS 94(10577–10582)1997.*
Pepinsky et al., Identification of a Palmitic Acid–modified Form of Human Sonic hedgehog. Journal of Biological Chemistry, May 29, 1998.*
Bumcrot DA et al., Mol. Cell. Biol. 15(4)2294–303, 1995.*
Bumcrot, et al., Proteolytic Processing Yields Two Secreted Forms of Sonic hedgehog, Molecular and Cellular Biology, vol. 15, No. 4, pp. 2294–2303 (1995).
Seytter, et al., Hydrophobic Modifications at the Amino–Terminal Cysteine of Recombinant Sonic Hedgehog Signaling Domain Dramatically Increase Activity. Bone, vol. 23, p. S563, Abstract (1998).
Pepinsky, et al., Identification of a Palmitic Acid–modified Form of Human Sonic Hedgehog, The Journal of Biological Chemistry, vol. 273, pp. 14037–14045 (1998).
Porter, et al., Cholesterol Modification of Hedgehog Signaling Proteins in Animal Development, Science, vol. 274, pp. 255–259 (1996).

Nakamura, et al., Induction of Osteogenic Differentiation by Hedgehog Proteins, Biochemical and Biophysical Research Communications, vol. 237, pp. 465–469 (1997).
Bumcrot, et al., Proteolytic Processing Yields Two Secreted Forms of Sonic hedgehog, Molecular and Cellular Biology, vol. 15, No. 4, pp. 2294–2303 (1995).
Miao, et al., Sonic Hedgehog Promotes the Survival of Specific CNS Neuron Populations and Protects These Cells from Toxic Insult In Vitro, The Journal of Neuroscience, vol. 17, No. 15, pp. 5891–5899 (1997).
Fietz, et al., The hedgehog gene family in Drosophila and vertebrate development, Development 1994 Supplement, pp. 43–51 (1994).
Hynes, et al., Induction of Midbrain Dopaminergic Neurons by Sonic Hedgehog, Neuron, vol. 15, pp. 35–44 (1995).
Hammerschmidt, The world according to hedgehog, TIG, vol. 13, No. 1, pp. 14–21 (1997).
Kinto, et al., Fibroblasts expressing Sonic hedgehog induce osteoblast differentiation and ectopic bone formation, FEBS Letters, vol. 404, pp. 319–323 (1997).
Cha, et al., Rhodopsin Kinase: Expression in baculovirus–infected insect cells, and characterization of post–translational modifications, Proc. Natl. Acad. Sci, vol. 94, pp. 10577–10582 (1997).
Asahina et al., 1996, "Human osteogenic protein–1 induces chondroblastic, osteoblastic, and/or adipocytic differentiation of clonal murine target cells", Exp. Cell. Res. 222:38–47.
Bitgood et al., 1996, "Sertoli cell signaling by Desert hedgehog regulates the male germline", Curr. Biol. 6:298–304.
Chiang et al., 1996, "Cyclopia and defective axial patterning in mice lacking Sonic hedgehog gene function", Nature 83:407–413.
Karaplis et al., 1994, "Lethal skeletal dysplasia from targeted disruption of the parathyroid hormone–related peptide gene", Genes Dev. 8:277–289.
Lai et al., 1995, "Patterning of the neural ectoderm of Xenopus laevis by the amino–terminal product of hedgehog autoproteolytic cleavage", Development 121:2349.
Perrimon, 1995, "Hedgehog and beyond", Cell 80:517–520.
Smith, 1994, "Hedgehog, the floor plate, and the zone of polarizing activity", Cell 76:193–196.
Vortkamp et al., 1996, "Regulation of rate of cartilage differentiation by Indian hedgehog and PTH–related protein", Science 273:613–622.
Wozney et al., 1993, "Bone morphogenetic proteins and their gene expression", *Cellular and Molecular Biology of Bone* (New York: Academic Press) pp. 131–167.

* cited by examiner

*Primary Examiner*—Yvonne Eyler
*Assistant Examiner*—Michael Brannock
(74) *Attorney, Agent, or Firm*—Ropes & Gray LLP

(57) ABSTRACT

The present invention provides isolated highly active hedgehog proteins esterified with a fatty acid having from 14 to 20 carbon atoms at the N-terminal domain of the protein. The highly active hh proteins are particularly useful therapeutic agents for treating bone disorders and neurodegenerative diseases. Methods for obtaining the highly active modified hedgehog proteins are also provided.

6 Claims, 16 Drawing Sheets

Human Sonic hedgehog amino acid sequence (SEQ ID No:1)

Amino Terminus:     MLLLARCLLLVLVSSLLVCSGLACGPGRGFGKRRHPKKLTPLAY

KQFIPNVAEKTLGASGRYEGKISRNSERFKELTPNYNPDIIFKDEENTGADRLMTQRC

KDKLNALAISVMNQWPGVKLRVTEGWDEDGHHSEESLHYEGRAVDITTSDRDRSKYGM

LARLAVEAGFDWVYYESKAHIHCSVKAENSVAAKSGGCFPGSATVHLEQGGTKLVKDL

SPGDRVLAADDQGRLLYSDFLTFLDRDDGAKKVFYVIETREPRERLLLTAAHLLFVAP

HNDSATGEPEASSGSGPPSGGALGPRALFASRVRPGQRVYVVAERDGDRRLLPAAVHS

VTLSEEAAGAYAPLTAQGTILINRVLASCYAVIEEHSWAHRAFAPFRLAHALLAALAP

ARTDRGGDSGGGDRGGGGGRVALTAPGAADAPGAGATAGIHWYSQLLYQIGTWLLDSE

ALHPLGMAVKSS       Carboxy-terminus

Figure 18

SEQUENCE LISTING

```
<160> NUMBER OF SEQ ID NOS: 1

<210> SEQ ID NO 1
<211> LENGTH: 462
<212> TYPE: PRT
<213> ORGANISM: Homo sapiens
<220> FEATURE:
<223> OTHER INFORMATION: Human Sonic hedgehog

<400> SEQUENCE: 1

Met Leu Leu Leu Ala Arg Cys Leu Leu Leu Val Leu Val Ser Ser Leu
 1               5                  10                  15

Leu Val Cys Ser Gly Leu Ala Cys Gly Pro Gly Arg Gly Phe Gly Lys
                20                  25                  30

Arg Arg His Pro Lys Lys Leu Thr Pro Leu Ala Tyr Lys Gln Phe Ile
        35                  40                  45
```

```
Pro Asn Val Ala Glu Lys Thr Leu Gly Ala Ser Gly Arg Tyr Glu Gly
     50                   55                  60

Lys Ile Ser Arg Asn Ser Glu Arg Phe Lys Glu Leu Thr Pro Asn Tyr
 65              70                  75                      80

Asn Pro Asp Ile Ile Phe Lys Asp Glu Asn Thr Gly Ala Asp Arg
             85                  90                  95

Leu Met Thr Gln Arg Cys Lys Asp Lys Leu Asn Ala Leu Ala Ile Ser
             100                 105             110

Val Met Asn Gln Trp Pro Gly Val Lys Leu Arg Val Thr Glu Gly Trp
         115             120                 125

Asp Glu Asp Gly His His Ser Glu Glu Ser Leu His Tyr Glu Gly Arg
 130             135                     140

Ala Val Asp Ile Thr Thr Ser Asp Arg Asp Arg Ser Lys Tyr Gly Met
145             150                 155                     160

Leu Ala Arg Leu Ala Val Glu Ala Gly Phe Asp Trp Val Tyr Tyr Glu
             165                 170                 175

Ser Lys Ala His Ile His Cys Ser Val Lys Ala Glu Asn Ser Val Ala
             180                 185             190

Ala Lys Ser Gly Gly Cys Phe Pro Gly Ser Ala Thr Val His Leu Glu
         195                 200             205

Gln Gly Gly Thr Lys Leu Val Lys Asp Leu Ser Pro Gly Asp Arg Val
 210                 215                 220

Leu Ala Ala Asp Asp Gln Gly Arg Leu Leu Tyr Ser Asp Phe Leu Thr
225             230                 235                     240

Phe Leu Asp Arg Asp Gly Ala Lys Lys Val Phe Tyr Val Ile Glu
             245                 250                 255

Thr Arg Glu Pro Arg Glu Arg Leu Leu Leu Thr Ala Ala His Leu Leu
             260                 265                 270

Phe Val Ala Pro His Asn Asp Ser Ala Thr Gly Glu Pro Glu Ala Ser
             275                 280                 285

Ser Gly Ser Gly Pro Pro Ser Gly Gly Ala Leu Gly Pro Arg Ala Leu
     290                 295                 300

Phe Ala Ser Arg Val Arg Pro Gly Gln Arg Val Tyr Val Val Ala Glu
305             310                 315                     320

Arg Asp Gly Asp Arg Arg Leu Leu Pro Ala Ala Val His Ser Val Thr
             325                 330                 335

Leu Ser Glu Glu Ala Ala Gly Ala Tyr Ala Pro Leu Thr Ala Gln Gly
             340                 345                 350

Thr Ile Leu Ile Asn Arg Val Leu Ala Ser Cys Tyr Ala Val Ile Glu
     355                 360                 365

Glu His Ser Trp Ala His Arg Ala Phe Ala Pro Phe Arg Leu Ala His
     370                 375                 380

Ala Leu Leu Ala Ala Leu Ala Pro Ala Arg Thr Asp Arg Gly Gly Asp
385             390                 395                     400

Ser Gly Gly Gly Asp Arg Gly Gly Gly Arg Val Ala Leu Thr
             405                 410                 415

Ala Pro Gly Ala Ala Asp Ala Pro Gly Ala Gly Ala Thr Ala Gly Ile
             420                 425                 430

His Trp Tyr Ser Gln Leu Leu Tyr Gln Ile Gly Thr Trp Leu Leu Asp
         435                 440                 445

Ser Glu Ala Leu His Pro Leu Gly Met Ala Val Lys Ser Ser
 450                 455                 460
```

ACTIVE MODIFIED HEDGEHOG PROTEINS

FIELD OF THE INVENTION

The Invention concerns an active form of a hedgehog protein, a process for its recombinant: production and its therapeutic use.

BACKGROUND OF THE INVENTION

Hedgehog (hh) proteins are understood as a family of secreted signal proteins which are responsible for the formation of numerous structures in embryogenesis (J. C. Smith, Cell 76 (1994) 193–196, N. Perrimon, Cell 80 (1995) 517–520, C. Chiang et al., Nature 83 (1996) 407, M. J. Bitgood et al., Curr. Biol. 6 (1996) 296, A. Vortkamp em al., Science 273 (1996) 613, C. J. Lai et al., Development 121 (1995) 2349). During its biosynthesis a 20 kD N-terminal domain and a 25 kD C-terminal domain are obtained after cleavage of the signal sequence and autocatalytic cleavage. The N-terminal fragment is modified in its natural form with cholesterol at its C-terminus (J. A. Porter et al., Science 274 (1996) 255–259). In higher life-forms the hh family is composed of at least three members i.e. sonic, indian and desert hh (Shh, Ihh, Dhh; M. Fietz et al., Development (Suppl.) (1994) 43–51). Differences in the activity of hedgehog proteins that were produced recombinantly were observed after production in prokaryotes and eukaryotes (M. Hynes et al., Neuron 15 (1995) 35–44 and T. Nakamura et al., Biochem. Biophys. Res. Comm. 237 (1997) 465–469.

Hynes et al. compare the activity of hh in the supernatant of transformed human embryonic kidney 293 cells (eukaryotic hh) with hh produced from *E. coli* and isolated from the cytoplasm and find a four-fold higher activity of hh from the supernatants of the kidney cell line. A potential additional accessory factor which is only expressed in eukaryotic cells, a post-translational modification, a different N-terminus since the hh isolated from *E. coli* contains 50% of a hh which carries two additional N-terminal amino acids (Gly-Ser) or is shortened by 5–6 amino acids, or a higher state of aggregation (e.g. by binding to nickel agarose beads) have been discussed to be the reason for this increased activity.

Nakamura et al. compare the activity of shh in the supernatant of transformed chicken embryo fibroblasts with an shh fusion protein isolated from *E. coli* which still has an N-terminal polyhistidine part. The shh in the supernatant of the fibroblasts has a seven-fold higher activity than the purified *E. coli* protein with regard to stimulation of alkaline phosphatase (AP) in C3H10T ½ cells. Molecules such as bone morphogenetic proteins (BMPs) have been discussed as the reason for the increased activity which are only present in the supernatant of eukaryotic cells and cause the stronger induction of AP.

Kinto et al., FEBS Letters, 404 (1997) 319–323 describe that fibroblasts which secrete hh induce ectopic bone formation in an i.m. implantation on collagen.

SUMMARY OF THE INVENTION

The object of the invention is to produce hh proteins (polypeptides) which have a considerably improved activity compared to the known forms. In accordance with the present invention, the highly active hh proteins are particularly useful for inducing or stimulating chondrocytes and osteocytes as well as for treating neurodegenerative diseases. Thus, the highly active hh proteins of the present invention are useful therapeutic agents for treating bone disorders such as, for example, osteoporosis and bone fractures.

In accordance with the present invention, a method is provided for obtaining isolated highly active post-translationally processed hedgehog protein derivative (hh derivative) which are esterified with a fatty acid having from 14 to 20 carbon atoms (i.e., $C_{14}$–$C_{20}$) at the N-terminal domain of the protein. The highly active hh proteins of the present invention are produced by expression of a gene which encodes a hedgehog protein using a baculovirus expression system in a fermentation medium capable of producing the esterified hedgehog protein wherein the fermentation period is up to 30 hours, preferably from about 24 to about 27 hours.

Isolation of the hh derivative from the fermentation supernatent can be obtained by conventional protein isolation techniques such as through binding of the hh protein to heparin-Sepharose and hydroxylapatite. Purification of the fermentation supernatant is preferably performed in the presence of a protease inhibitor and a non-ionic detergent

BRIEF DESCRIPTION OF THE DRAWINGS

FIG. 18 shows the amino acid sequence of human sonic hedgehog.

DETAILED DESCRIPTION OF THE INVENTION

Figure 1:
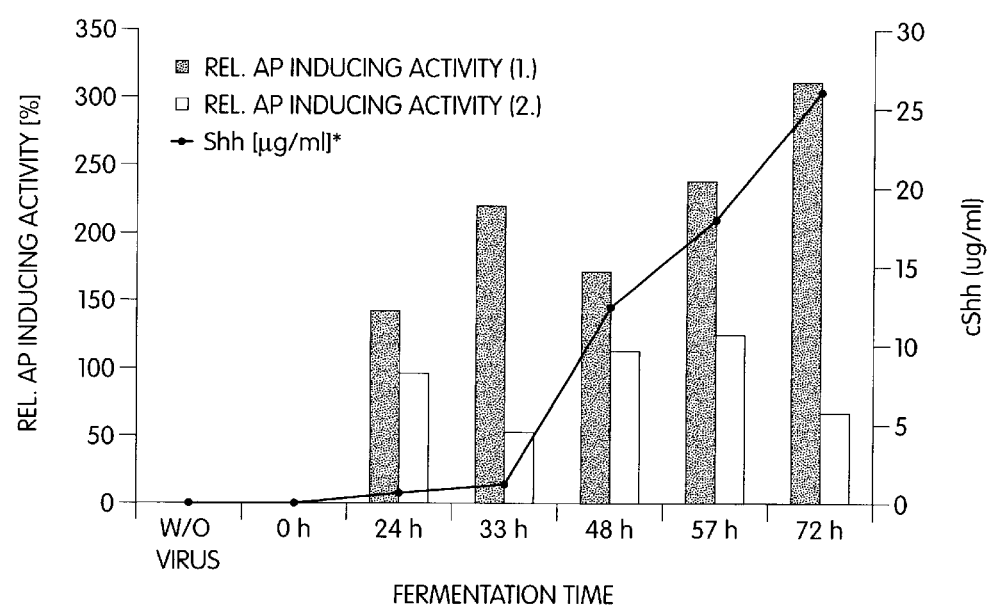
FIG. 1 is a plot showing the kinetics of the secretion of alkaline phosphatase (AP) inducing activity (bars) and shh protein (dots and line) by High Five cells after infection with baculovirus (t=0).
Figure 2:
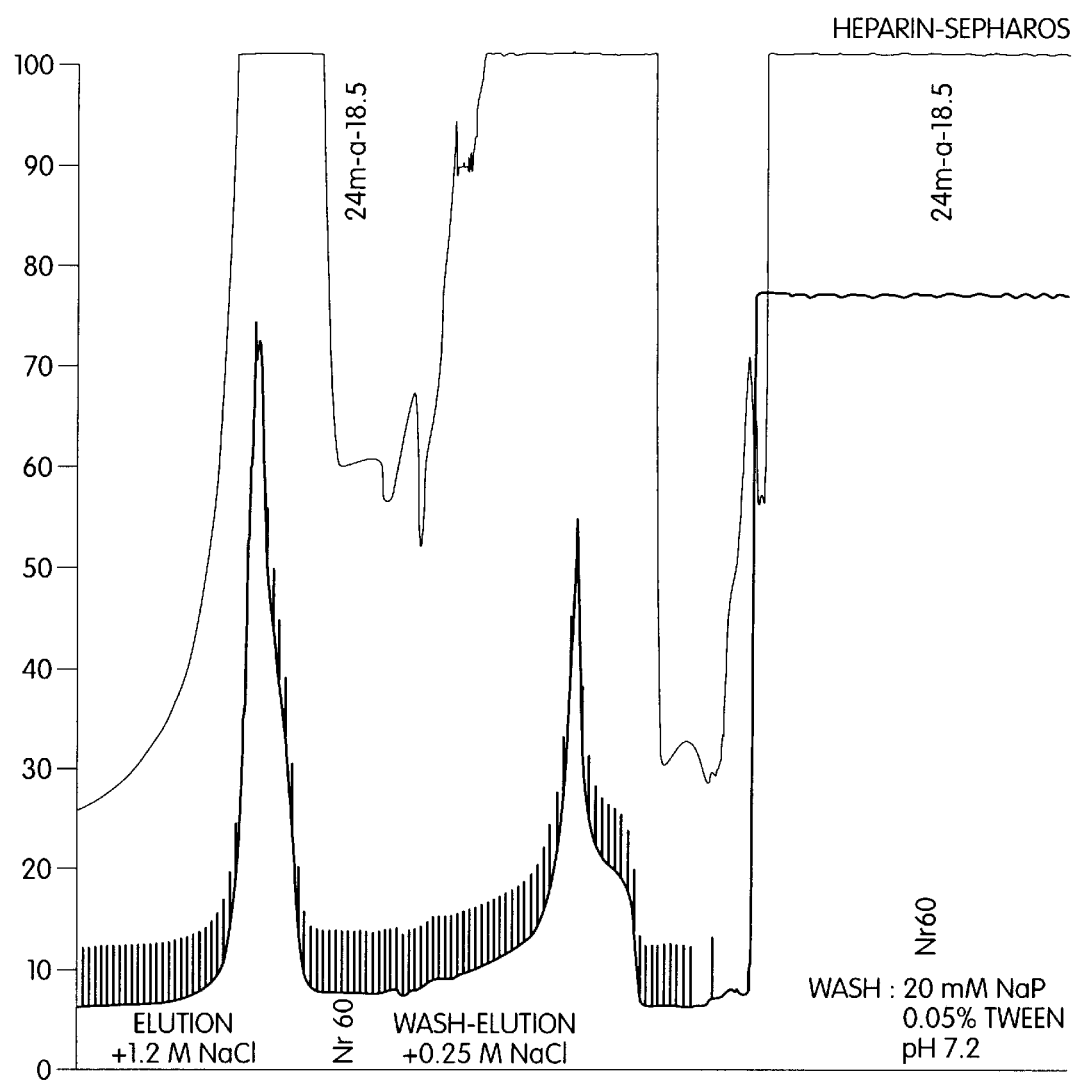
FIG. 2 is an elution diagram of the purification of the fermentation supernatant with heparin-Sepharose.
Figure 3:
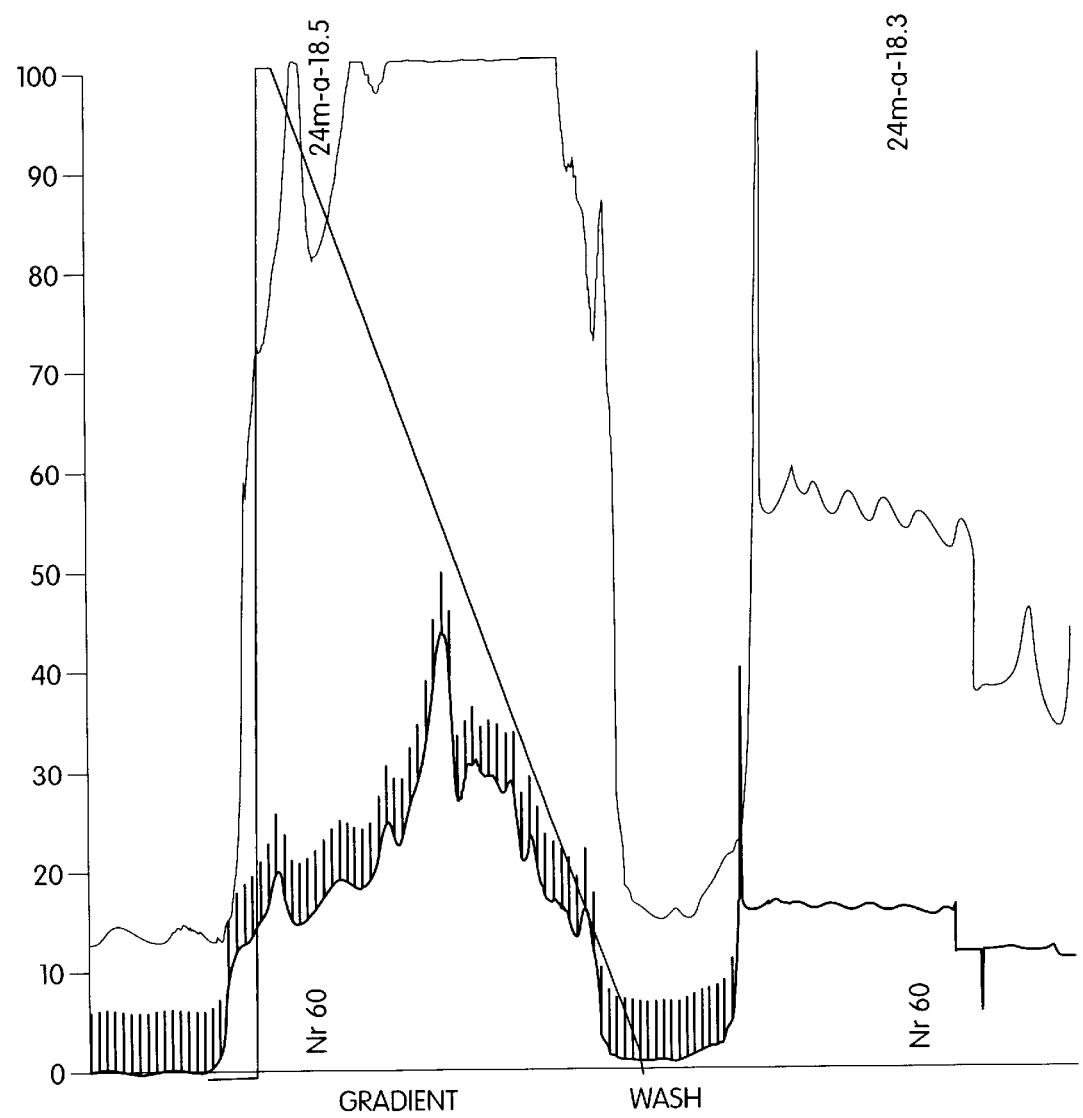
FIG. 3 is an elution diagram of the purification of the dialyzed eluate of the heparin-Sepharose with hydroxylapatite.
Figure 4:
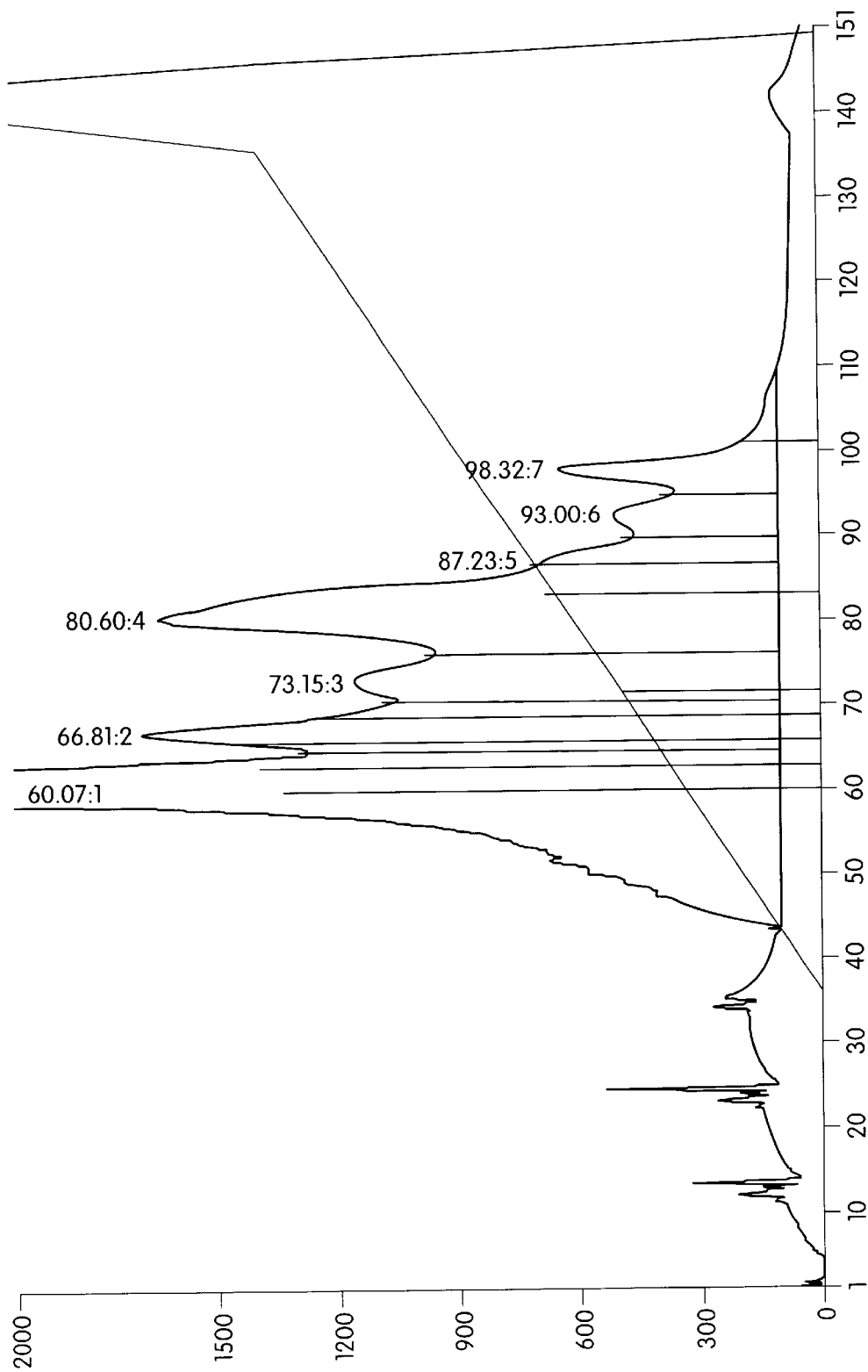
FIG. 4 is an elution diagram of the purification of the dialyzed active fractions of the hydroxylapatite column with a 1 ml HiTrap heparin column.
Figure 5:
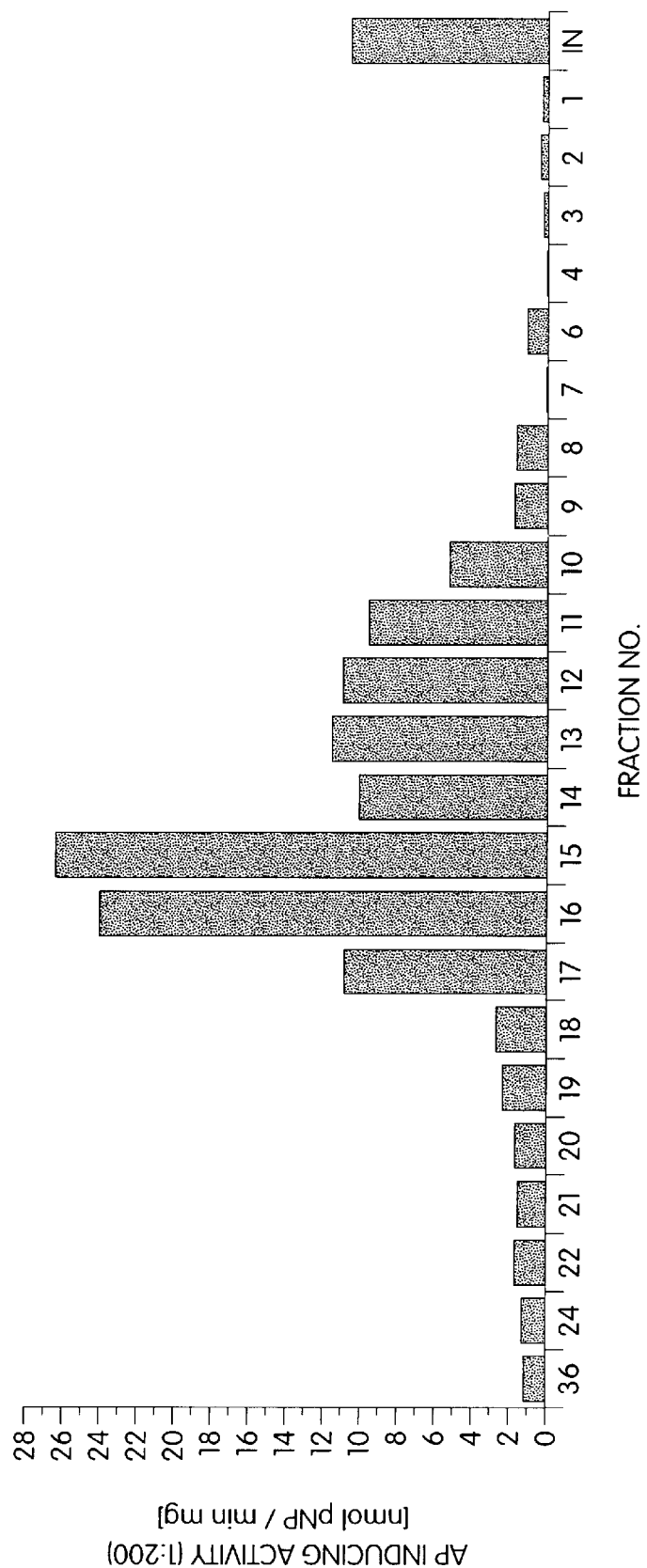
FIG. 5 shows the alkaline phosphatase inducing activity of the fractions of the 1 ml High Trap heparin chromatography.
Figure 6:
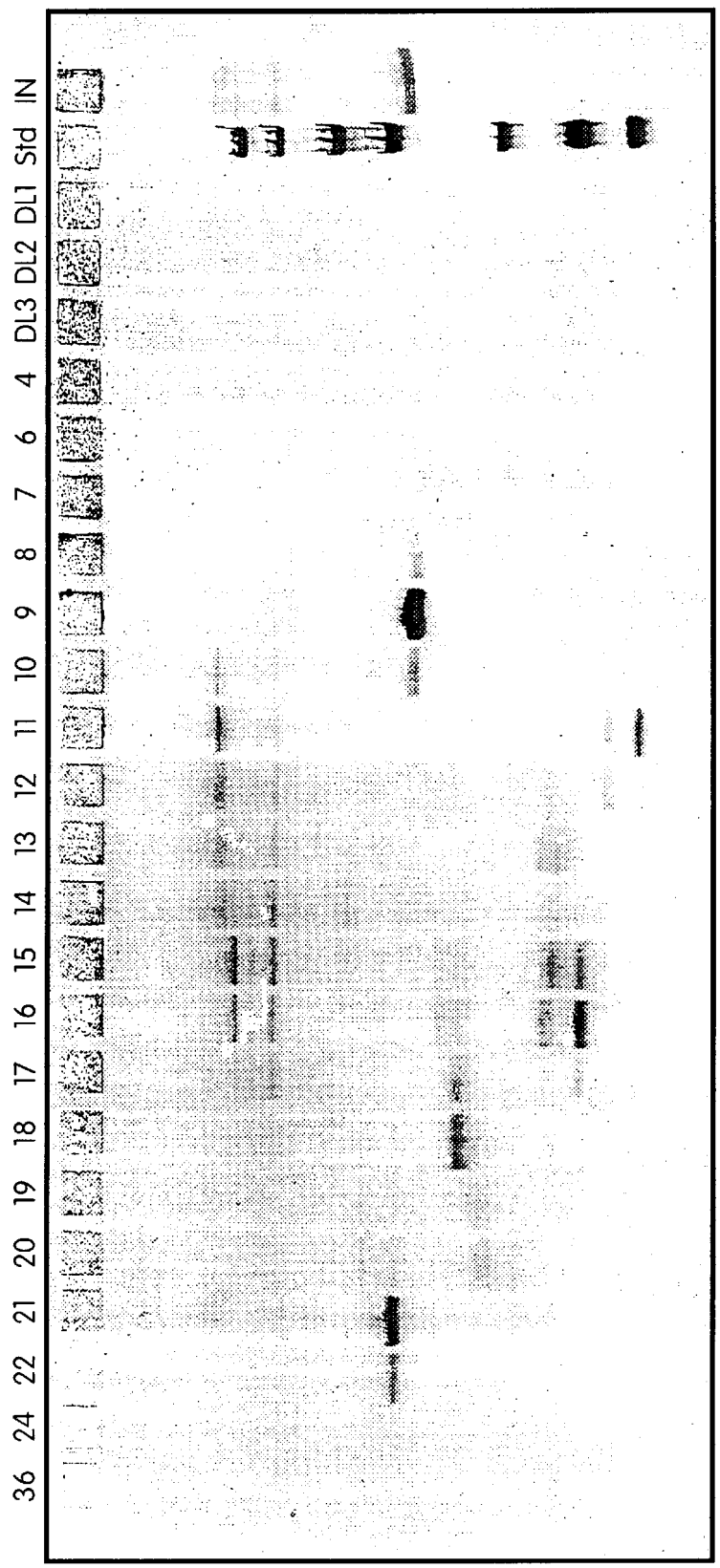
FIG. 6 shows coomassie staining of SDS-PAGE with alkylated fractions of the 1 ml High Trap heparin chromatography.
Figure 7:
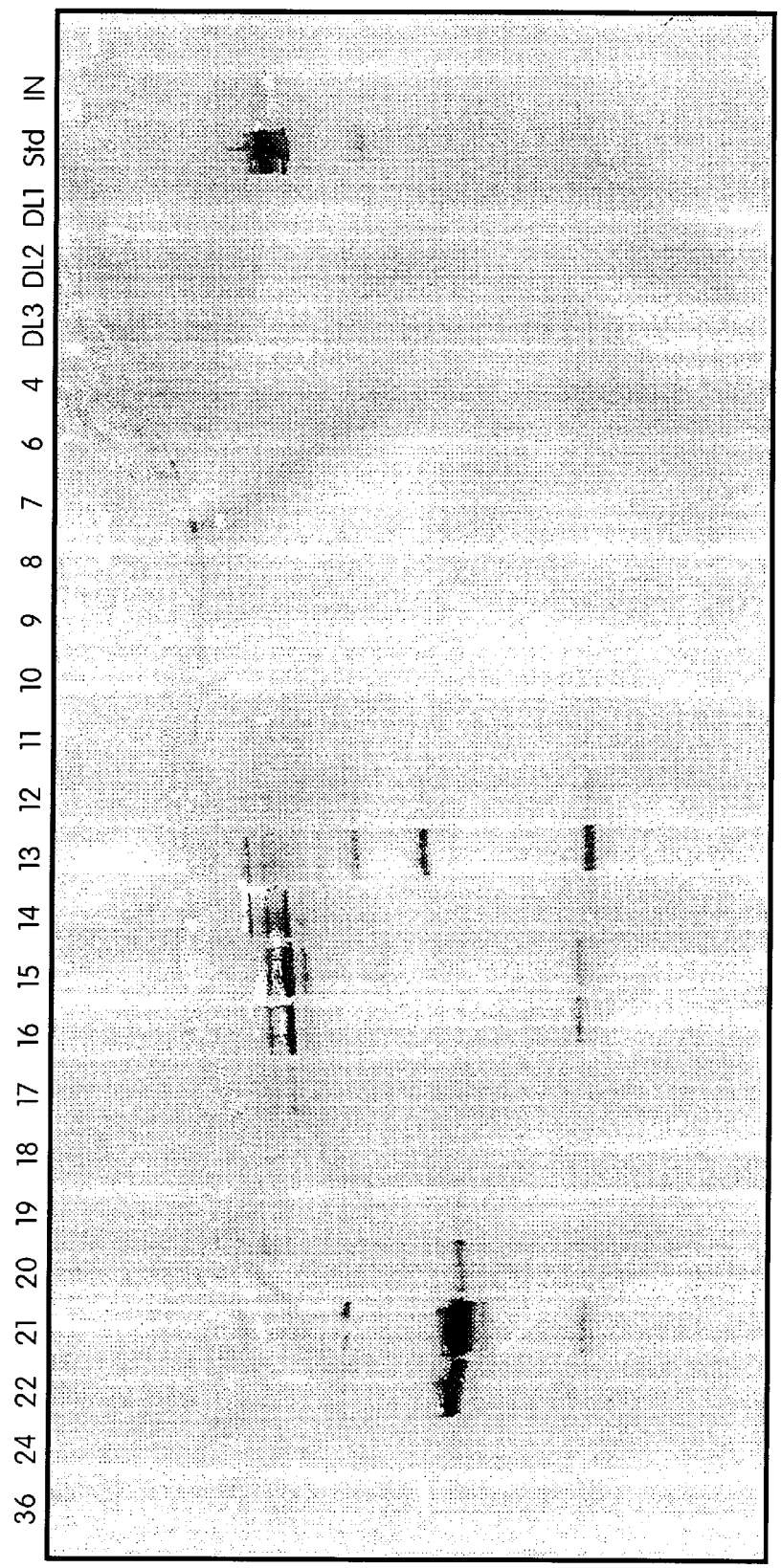
FIG. 7 is a Western blot with an antibody against the N-terminus of shh of the SDS-PAGE with alkylated samples of the fractions of the 1 ml High Trap heparin chromatography.
Figure 8:
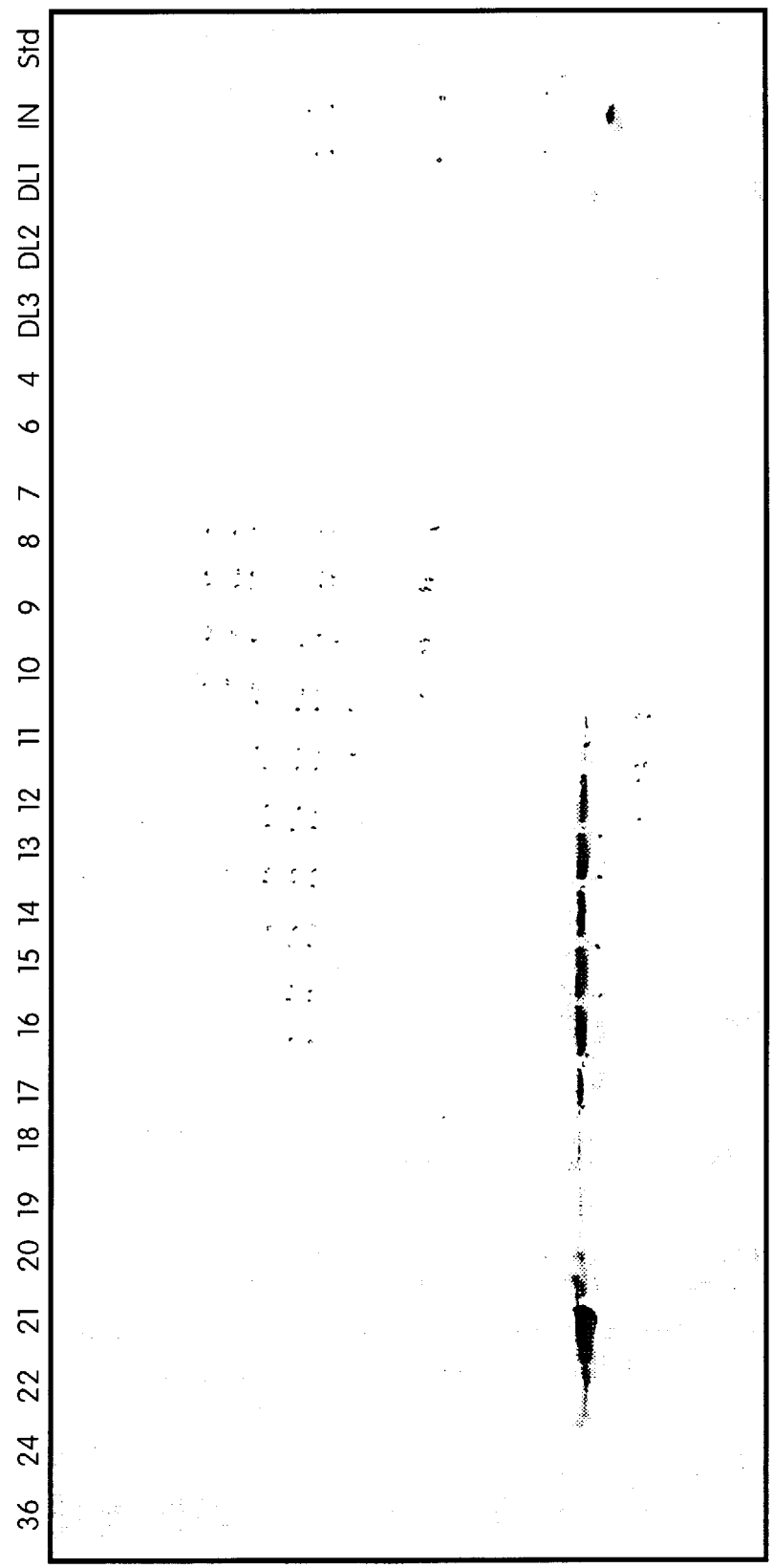
FIG. 8 is a Western blot with an antibody against the N-terminus of shh of the SDS-PAGE with reducing samples of the fractions of the 1 ml High Trap heparin chromatography.
Figure 9:
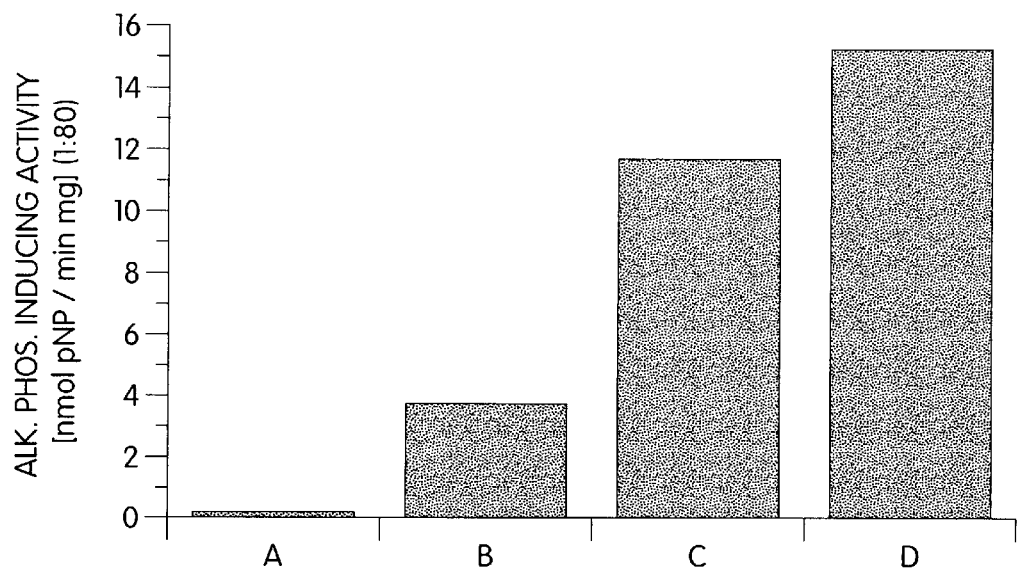
FIG. 9 shows the influence of suramin on the activity of the hh derivative: No suramin (B), suramin ad 0.1 mg/ml only added after dialysis against PBS+0.05% Tween®80 or (C) suramin ad 0.1 mg/ml added before dialysis and dialysed against PBS+0.05% Tween®80 containing additionally 0.1 mg/ml suramin (D) were added to aliquots of an active fraction after hydroxylapatite chromatography. The AP activity in the absence of hh is shown by (A).
Figure 10:
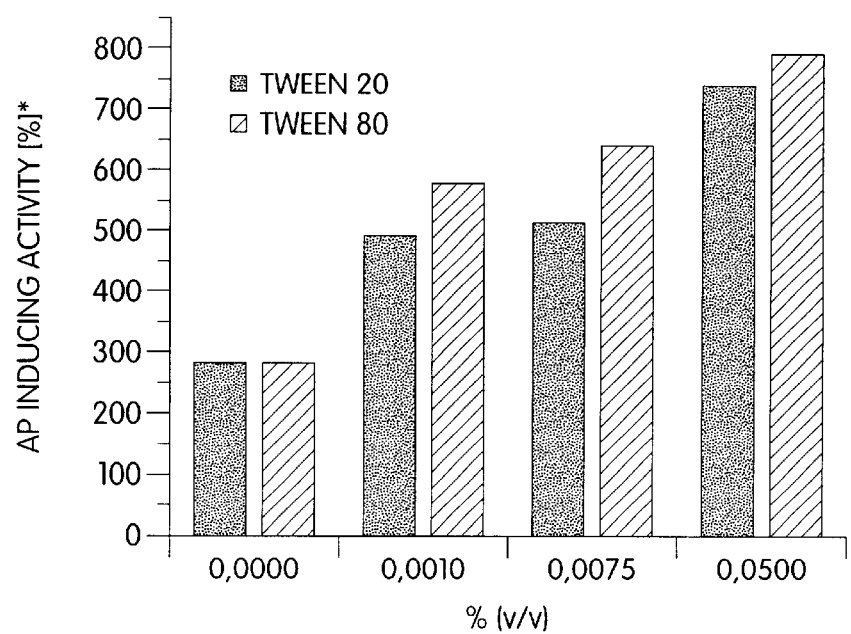
FIG. 10 shows the influence of Tween®20 and Tween®80 on the activity of the hh derivative: Aliquots of a pool of AP active fractions after SP Sepharose chromatography in 50 mM NaPi, 0.9 M NaCl, 1 mM EDTA pH 7.3 were admixed with the stated concentrations of Tween and dialysed against PBS containing the respective concentration of Tween. The samples were sterile filtered through 0.2 μm filters before being used in the C3H10T1/2 test.

The present invention provides isolated highly active hedgehog proteins having a molecular weight of from about 19 to about 26 kD which are esterified with a fatty acid having from 14 to 20 carbon atoms at the N-terminal domain of the protein. Esterification of the hedgehog protein with a $C_{16}$ fatty acid is preferred.

In accordance with the present invention, the highly active hh proteins are particularly useful for inducing or stimulating chondrocytes and osteocytes as well as for treating neurodegenerative diseases. Thus, the highly active hh proteins of the present invention are useful therapeutic agents for treating bone disorders such as, for example, osteoporosis and bone fractures.

The method of the present invention for producing the highly active hedgehog proteins esterified with a fatty acid having from 14 to 20 carbon atoms comprises (a) providing an insect cell containing a baculovirus vector having a gene inserted therein capable of expressing a hedgehog protein, and a fermentation medium such that the insect cell and medium are capable upon fermentation of producing a fatty acid having from 14 to 20 carbon atoms; (b) fermenting the insect cell in the medium for a period of about 30 hours or less to produce the fatty acid and express the hedgehog protein esterified with the fatty acid; and (c) isolating the esterified hedgehog protein from the protein produced during the fermentation.

Any fermentation conditions which allow the esterification of the hedgehog protein with a fatty acid having from 14 to 20 carbon atoms can be utilized. Preferably, the fermentation period is from about 24 to about 27 hours. Generally, the fermentation is carried out at from about 10 to 35° C. and pH of about 4 to 8. Fermentation at room temperature and neutral pH is preferred. Any conventional medium for fermentation of the baculovirus expression system that allows the esterification of the hh protein can be utilized. A preferred fermentation medium is Excell 400 medium (JHR, Inc.).

Isolation of the esterified hh protein can be obtained by conventional techniques for isolation of proteins such as through binding of the hh protein to heparin-Sepharose and hydroxylapatite. The hedgehog proteins of the present invention can be further purified by techniques such as anion or cation exchange chromatography and reverse-phase HPLC. Purification of the cell supernatant is preferably performed in the presence of a protease inhibitor and a non-ionic detergent.

Hedgehog proteins are known and any hedgehog protein can be modified in accordance with this invention to esterify the protein at the N-terminal domain with a fatty acid having from 14 to 20 carbon atoms and in so doing provide the highly active hh proteins of the present invention.

The esterified hedgehog proteins of the present invention have the following characteristics:

exhibit an apparent molecular weight of 22±2 kDa under alkylating conditions in SDS-PAGE, exhibit an apparent molecular weight of 24±2 kD under reducing conditions in SDS-PAGE, are stabilized with respect to its activity by suramin are inactivated when 8 or more amino acids are cleaved N-terminally are inactivated by 90% or more when incubated with 10 mmol/l 1.4 dithioerythritol (DTE) for 2.5 hours at preferably pH 8 and 37° C., induce an activity for alkaline phosphatase of ca. 90 nmol pNP/min/mg at a concentration of 5 nmol/l in the presence of suramin, are not modified by cholesterol (C-terminal) and have at least 50-fold activity compared to the recombinant hh protein isolated from the cytoplasm of *E. coli*. Activity within the sense of the invention is understood as the activity of alkaline phosphatase which the polypeptide can induce in mammalian cells (activity in the alkaline phosphatase test). In this method a mouse fibroblast cell line is cultured in a medium which contains foetal calf serum. Subsequently sterile filtered sample is added, the cells are lysed after ca. 5 days and alkaline phosphatase is determined in the cell lysate by means of the cleavage of a chromogenic substrate (pNP, p-nitrophenol) (J. Asahina, Exp.Cell. Res. 222 (1996) 38–47 and T. Nakamura (1997)).

A baculovirus expression system is understood as an expression system composed of a baculovirus vector and an insect cell as the host cell. Such expression systems are known to a person skilled in the art and are for example described by Bumcrot (1995) for hh proteins. Preferred insect cells for use in obtaining the esterified hedgehog proteins of the present invention are High five cells.

A hedgehog protein is understood by the invention as a secreted signal protein which is responsible for the formation of numerous structures in embryogenesis. Sonic, indian or desert hh proteins are particularly preferably used (M.

Fietz et al. (1994). A hh protein with a sequence as described in the EMBL database under the No. L38518 is preferably used. Proteins of the hedgehog family exhibit a pronounced homology in their amino acid sequence which is why it is also preferable to express those nucleic acids which code for hedgehog proteins which are 80% or more homologous with the above-mentioned sequence of sonic hedgehog protein.

The human sonic hedgehog precursor protein is composed of the amino acids 1–462 of the sequence described in the EMBL database under No. L38518 (SEQ ID NO:1) (See FIG. 1). The amino acids 1–23 represent the signal peptide, the amino acids 24–197 represent mature signal domain, the amino acids 32–197 represent the signal domain shortened by 8 amino acids and the amino acids 198–462 represent the auto-processing domain after autoproteolytic cleavage. Thus, amino acids 24–197 of the human sonic hedgehog protein described in EMBL database sequence No. L38518 (SEQ ID NO:1) (See FIG. 1) represent the N terminal domain of this sequence.

The first 8 amino acids of the hedgehog proteins of the present invention are the first 8 amino acids of the processed hedgehog protein, for example, the amino acids Cys24-Gly31 of the sequence described in the EMBL database under No. L38518 for sonic hedgehog protein. Since the modified group can be cleaved with the first N-terminal amino acids of hedgehog protein and the activity is greatly reduced by incubation with hydroxylamine or DTE, the binding of the group is localized on these amino acids preferably in the form of a thioester, preferably as palmitic acid thioester, on the cysteine which is present in the first eight amino acids of the hedgehog protein.

Surprisingly when preferably the N-terminal domain of hedgehog protein is produced recombinantly in the baculovirus expression system, a highly active form of the protein (activity increased by at least 10-fold, preferably at least 100-fold compared to recombinant shh from the cytoplasm of E. coli) accumulates in the initial period of the fermentation. However, overall the amount of highly active hh derivative according to the invention is only about 0.2–5% of the total protein in the supernatant of the cells after expression in the baculovirus expression system. This derivative of the polypeptide according to the invention can be in particular isolated when the fermentation is terminated at the latest after about. 30 hours or less, preferably after about 24–27 hours. This is also surprising since a fermentation period after infection of at least 2 days has been previously described for the production of hh proteins in the baculovirus expression system (Bumcrot et al., Mol. Cell. Biol. 15 (1995) 2294–2303). It has also been described for other proteins which are produced in the baculovirus system such as rhodopsin kinase (Cha et al., Proc. Natl. Acad. Sci. USA 94 (1997) 10577–10582) that a maximum of protein and activity is achieved after 64–88 h. According to the invention it was found for hedgehog proteins that although the amount of hedgehog protein in the fermentation supernatant greatly increases in the period between 33 and 72 hours, mainly hh protein with an activity that is known from the prior art is formed in this period. In contrast the amount of such a hh protein is considerably less (at least 3–5-fold) when the fermentation period is reduced to below ca. 30 h. which allows the identification and isolation of the highly active hh protein derivative according to the invention.

The molecular weight of the derivative according to the invention is 19,796.7±2 D when analysed by means of MALDI mass spectroscopy and is increased by 236.7±2 D compared to unmodified hh protein (cytoplasmically expressed hh protein in E. coli), corresponding to the molecular weight of a palmitic acid thioester. The hydrophobic modification increases the mobility in SDS-PAGE by increased SDS binding so that apparently a lower molecular weight is seen under alkylating conditions (derivatized hh protein) than under strongly reducing conditions (hh protein without derivatization). The accuracy of the molecular weight determination in SDS-PAGE is also about ±1–2 D.

After purification with heparin-Sepharose, hydroxylapatite and porous HSM ion exchanger chromatography, the hh derivative according to the invention has an activity measured via the induction of alkaline phosphatase in a cell test (activity in the AP cell test) which is increased by at least 50-fold, preferably by at least 100-fold and particularly preferably by at least $10^3$ to $10^6$-fold compared to soluble hh protein expressed in the cytoplasm of E. coli. Such an active hh derivative is not modified by cholesterol like the N-terminal hh fragment described by J. A. Porter since only the N-terminal and not also the C-terminal auto processing domain was expressed. The hh derivative according to the invention is present in a biologically active three-dimensional structure. Consequently the invention for the first time enables the isolation of highly active hedgehog protein and provides a general, reproducible method for the production and characterization of highly active hedgehog proteins.

Hence the invention concerns hedgehog proteins with an at least 100-fold, preferably at least $10^3$ to $10^6$-fold increased activity compared to the corresponding hedgehog protein which was isolated from the cytoplasm of E. coli were the activity is determined by the induction of alkaline phosphatase in the cell test.

A corresponding hedgehog protein which is produced in the cytoplasm of E. coli is understood according to the invention as a hedgehog protein which is isolated in a soluble form in the cytoplasm after expression in E. coli. In this process a vector is used as the expression vector which contains a nucleic acid to be expressed which codes for a hedgehog protein of the same amino acid sequence as the nucleic acid to be expressed of the expression vector which is used for expression in the baculovirus expression system. However, in this process it may be expedient to change one or other amino acid in the baculovector or E. coli vector in order to for example improve the expression or the solubility. However, for the comparison of activities of the hedgehog protein according to the invention with the E. coli protein it is expedient to use expression vectors for identical proteins. The hh protein that is formed in this process is not post-translationally modified (no derivatization with cholesterol etc.).

The hh derivative according to the invention is very sensitive towards proteases which is why it is preferable to add protease inhibitors such as for example aprotinin, EDTA (up to 1 mmol/l), PMSF or pepstatin or a mixture thereof to the supernatant of the fermentation.

Furthermore it is preferable to add non-ionic detergents such as polysorbate (e.g. Tween®20, Tween®80, Triton®X100) during the purification, preferably before or after the first crude purification over heparin-Sepharose. Since this also stabilizes the hh proteins according to the invention.

In a first step for the purification of the protein according to the invention it is expedient to carry out a chromatography on heparin-Sepharose. It is preferable to carry out this chromatography as a step elution i.e. preferably to elute at a concentration of at least 0.7 mol/l NaCl (preferably 1.2 mol/l) after washing with 250 mmol/l NaCl.

It is particularly preferable to carry out a hydroxylapatite chromatography to purify the hh derivative according to the invention. This achieves a good concentration of the activity with relatively low losses (<50%). Further suitable chromatographic steps are for example a heparin-Sepharose chromatography (Miao et al., J. Neurosci. 17 (1997) 5891–5899) which is, however, preferably carried out in the presence of non-ionic detergents. Furthermore it is preferable to carry out a dialysis after the heparin-Sepharose chromatography in which it is particularly preferable that in this dialysis the pH value of the buffer is at least pH 5, in particular pH 6.5–7.5 and the ionic strength of the buffer corresponds to a solution of 1–20 mM sodium phosphate and 10–100 mM NaCl in particular 50 mM NaCl and the dialysis is carried out at a low concentration of total protein (1 mg/ml or less, preferably 0.5 mg/ml or less).

Furthermore, it is also preferable to add suramin during the purification or at least before determining the activity of the protein. The activity can also be stabilized by adding serum albumin (at least 50 μg/ml to 5 mg/ml) to the sample before dilution in the cell test. This also stabilizes the activity. In the case of suramin it was previously only known that it is suitable for detaching hh proteins from the cell surface or the extracellular matrix (Bumcrot et al., see above).

Furthermore, it is known that suramin inhibits the activity of growth factors (Middaugh et al., Biochem. 31 (1992) 9016–9024). Surprisingly it was found that the activity of hh proteins is increased by adding suramin.

For the further purification it is preferable to repeat chromatography on heparin-Sepharose and hydroxylapatite.

For the further purification it is additonally preferable to carry out an ion exchange chromatography with porous HS/M and/or Poros-Q (Boehringer Mannheim GmbH, DE) and preferably subsequently a RP-HPLC. In contrast to other ion exchanger media, only low losses of activity and a good separation of the active hh form is observed with Poros exchangers.

In a further embodiment of the invention the hh derivative according to the invention can be used to produce a pharmaceutical composition which is also a subject matter of the invention. This pharmaceutical composition contains a pharmacologically effective dose of the protein according to the invention and can be administered systemically as well as locally. It is also preferable to use the proteins according to the invention in combination with other proteins of the hedgehog family or bone growth factors such as bone morphogenetic proteins (BMPs), (Wozney et al., Cell. Mol. Biol. of Bone, Bone Morphogenetic Proteins and their Gene Expression, 131–167, Academic Press Inc. 1993) or parathyroid hormones (Karablis et al., Genes and Development 8 (1994) 277–289).

The protein according to the invention can be used advantageously to induce or stimulate chondrocytes and osteocytes in an osteoinductive pharmaceutical composition as well as to treat neurodegenerative diseases. Osteoinductive pharmaceutical compositions are for example known from the U.S. Pat. No. 5,364,839, WO 97/35607, WO 95/16035.

When the protein according to the invention is administered locally it is preferable to use it in combination with a suitable matrix as a carrier and/or with a sequestering agent. Such a matrix is suitable for slowly releasing the protein in vivo in an active form in particular in the vicinity of bone and cartilage. The sequestering agent is a substance which facilitates administration for example by injection and/or prevents or at least delays migration of the protein according to the invention from the site of administration.

A biocompatible degradable material for example based on collagen or other polymers based on polylactic acid, polyglycolic acid or co-polymers of lactic acid and glycolic acid are particularly suitable as a matrix material. Such polymer matrices are described for example in WO 93/00050.

Sequestering agents are for example cellulose and cellulose-like materials and for example alkyl cellulose, carboxymethyl cellulose, hyaluronic acid, sodium alginate, olyethylene glycol and polyvinyl alcohol of which hyaluronic acid is particularly preferred especially in a pharmaceutical composition even without carrier matrix.

It is also preferable for the production of the pharmaceutical composition to add auxiliary substances such as mannitol, sucrose, lactose, glucose or glycine and antioxidants such as EDTA, vitamin C, citrate and detergents, preferably non-ionic detergents like polysorbates and polyoxyethylenes. A pharmaceutical composition which is buffered in the pH range 4–8 is also preferred.

In a further preferred embodiment a pharmaceutical composition of the hedgehog protein according to the invention together with suramin and/or serum albumin is preferred and this is advantageously used.

The following example, publications and figures further elucidate the invention, the protective scope of which results from the patent claims. The described methods are to be understood as examples which still describe the subject matter of the invention even after modifications.

EXAMPLE 1

Expression of Recombinant Human Sonic hh (shh)

The N-terminal domain of human shh with the amino acids 24–197 (EMBL accession No. L 38518) was expressed with the N-terminal signal peptide 1–23 as described by Miao (J. Neurosci. (1997) 17, 5891–5899) and Bumcrot et al., (Mol. Cell. Biol. (1995) 15, 2294–2303) for the rat protein by means of recombinant baculovirus in High Five cells (Invitrogen, Leek, NL, Order No. E 855-02) using Excell 400 medium (JHR, Inc.) in which sufficient virus was used to infect each cell on average with one virus (multiplicity of infection (m.o.i.):1).

The fermenter contents were clarified after 26 or 72 h by centrifugation at 1000 g and filtration and the supernatant or the permeate was stored at −80° C. until further use. Fermentation samples were analysed for their content of alkaline phosphatase inducing activity [Nakamura et al. (1997), Kinto et al. (1997) FEBS Lett. 404, 319–323] and for their content of shh protein by means of RP-HPLC (Vydac C18, gradient of 0–90% acetonitrile in 0.1% trifluoroacetic acid, TFA) or SDS-PAGE.

In the preferred process the fermentation was terminated after 24–32 h (preferably after 24–27 h) fermentation time and the supernatant was clarified.

EXAMPLE 2

Purification of the Active hh Mutant on Heparin-Sepharose and Hydroxyapatite

1 Tablet of "complete" inhibitor mix (Boehringer Mannheim GmbH, order No. 1873580) was added per 50 ml supernatant to the clarified supernatant after thawing and 3.5 l of this solution was applied at 4° C. to a heparin-Sepharose column (volume 90 ml; Pharmacia Biotech) which had previously been equilibrated with 20 mM sodium phosphate, pH 7.2. After the sample application it was washed with 20 mM sodium phosphate, 0.05% Tween®80, pH 7.2 (=buffer A) and unspecifically bound protein was eluted by a wash step with buffer A which additionally contained 0.25 M NaCl. The activity was obtained by a subsequently elution with buffer A which additionally contained 1.2 M NaCl.

This eluate was subsequently diluted with one volume 10 mM sodium phosphate, 0.05% Tween®80, 50 mM NaCl, pH 7.2 (=buffer B) and dialysed against buffer B at 4° C.

The dialysate was applied to a hydroxyapatite column (volume 10 ml; Makro Prep; 40 μm, type I; BIO-Rad) equilibrated with buffer B. It was eluted with a gradient of 10 to 300 mM NaP in buffer B (2×200 ml).

Aliquots of the fractions were analysed for their ability to stimulate alkaline phosphatase in a mouse fibroblast cell line e.g. C3H10T1/2 cells as well as by means of SDS-PAGE and RP-HPLC. The remainder of the fractions was stored at −80° C. until further processing. The maximum activity elutes at the end of the gradient between 0.25–0.3 M sodium phosphate whereas inactive or only weakly active forms of shh already elute much earlier from the column.

The active fractions were pooled and dialysed against buffer B at 4° C. and applied to a 1 ml HiTrap heparin column (Pharmacia Biotech) which had been equilibrated with 20 mM potassium phosphate, 0.05 Tween®80, pH 7.2. It was eluted by a gradient of 20–1400 mM KCl in 20 mM potassium phosphate, 0.05% Tween®80, 50 mM NaCl, pH 7.2. Active fractions were identified by the stimulation of alkaline phosphatase in C3H10T1/2 cells, and alkylated and reduced samples were analysed by means of SDS-PAGE and Western blot with an antibody against the N-terminus of shh.

EXAMPLE 3

Purification of the Active hh Derivative on a Cation Exchanger and RP-HPLC (1) Purification by Cation Exchange Chromatography on PorosHS/M:

The active fractions after the hydroxylapatite or HiTrap heparin chromatography of example 1 were pooled and dialysed against 50 mM potassium phosphate, 0.05%. Tween®80, pH 7.2 (=buffer C) and applied to a 1.7 ml Poros®HS/M column (Boehringer Mannheim GmbH, GER) which had been equilibrated in buffer C. It was eluted by a gradient of 40 column volumes of 50–1000 mM KCl in buffer C and at a flow rate of 3 ml/min. Active fractions were identified by stimulation of alkaline phosphatase in C3H10T1/2 cells. The active fractions eluted at a salt concentration of ca. 400–700 mM KCl and the alkylated samples had a purity of ca. 50% in the SDS-PAGE under alkylating conditions whereas the major portion of the proteins already eluted at a salt concentration of ca. 80–400 mM KCl. It is possible to identify the highly active hh derivative contained in these fractions by subsequent RP-HPLC and mass analysis of the elution peak or by an appropriate analysis of the gel bands in the SDS-PAGE with a molecular weight of ca. 22 kD.

(2) Purification by RP-HPLC:

Active fractions of the Poros®-HS/M chromatography were further purified by RP-HPLC. For this 3.2 ml of a highly active fraction was applied to a 2.1×150 mm butyl column (Vydac™ 214TP5215) which had been equilibrated in 20% acetonitrile, 0.1% trifluoroacetic acid (TFA). It was eluted at 25° C. in a gradient of 20–90% acetonitrile in 0.1% TFA and analysed by detecting the absorbance at 220 nm and 280 nm. In comparison to weakly active unmodified monomeric or dimeric hh forms, the concentrated highly active hh derivative did not elute until a somewhat higher concentration of acetonitrile (ca. 41.2%). This species was collected and its mass was determined by MALDI mass spectrometry.

(3) Mass Analysis of the Active hh Derivative After RP-HPLC

Figure 17:
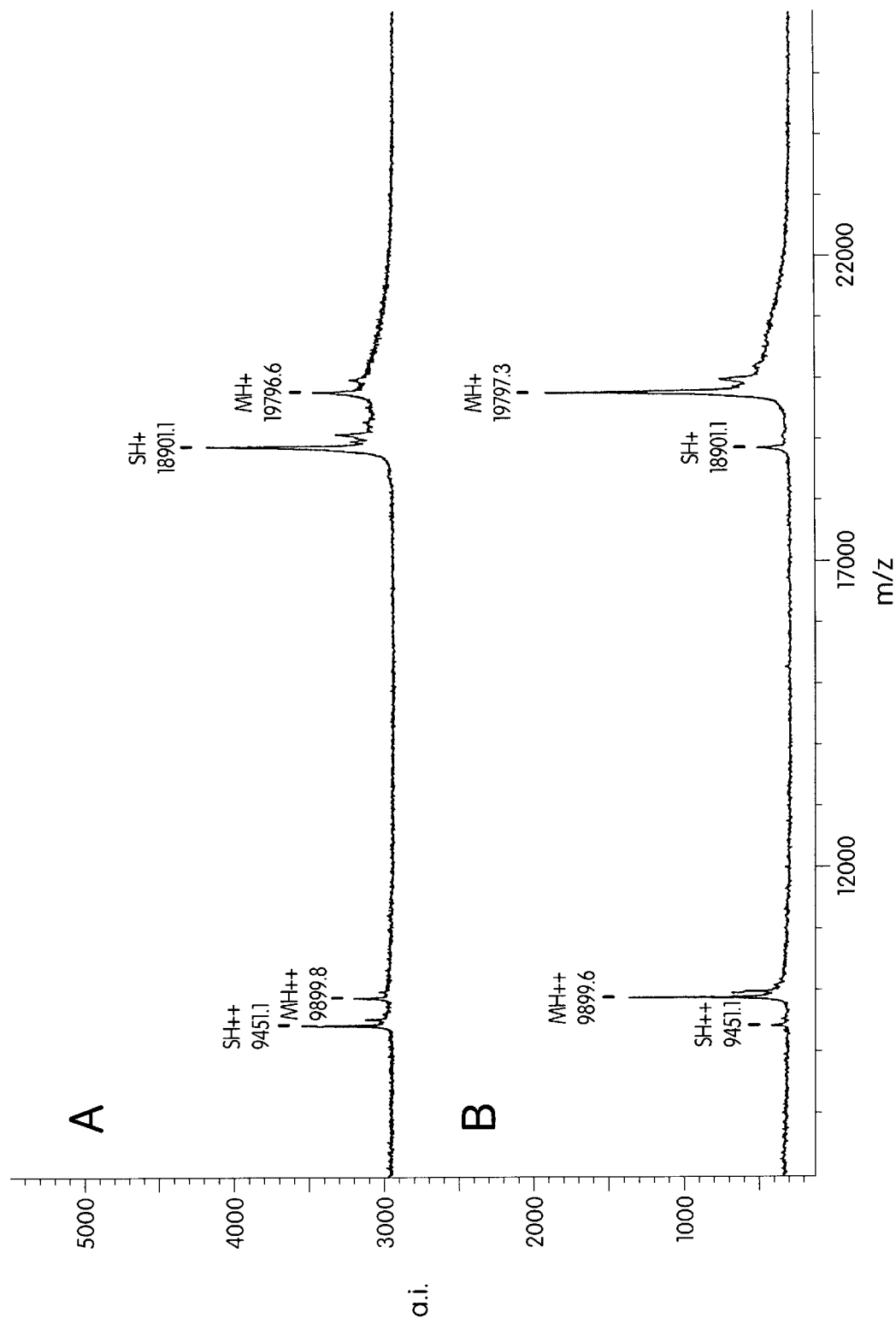
FIG. 17 shows MALDI mass spectra of the active modified hh derivative after RP-HPLC. A, B: Spectra obtained with different laser energies and from different spots.

For the mass analysis the RP eluate described above (total volume 200 μl) was admixed with 5 μl 25 mM sinapinic acid in 30% (w/w) acetonitrile/70% water/0.1% trifluoro-acetic acid, evaporated to dryness in a Speedvac concentrator and dissolved in 5 μl 30% (v/v) acetonitrile/70% water/0.1% trifluoroacetic acid. 1 μl of the solution obtained in this manner (referred to as solution A in the following) was mixed with 1 μl 25 mM sinapinic acid in 30% (v/v) acetonitrile/70% water/0.1% trifluoroacetic acid, applied to the target, dried in laboratory air and after drying it was measured in a Bruker REFLEX MALDI mass spectrometer with a so-called delayed extraction source. Only one molecular species was detected in the mass spectrum obtained in this manner apart from alkali and matrix adducts. Since the determination of the molecular mass without using an internal standard is only ±0.03%, the mass spectrum of an aliquot of solution A to which a protein of a known mass had been added was measured in addition to the mass spectrum of the pure solution A. For this 0.5 μl of solution A, 0.5 μl of an equivalently prepared solution of a shortened hedgehog molecule with an average molecular weight of 18900.1 D and 1 μl 25 mM sinapinic acid in 30% (v/v) acetonitrile/70% water/0.1% trifluoroacetic acid were mixed, applied to the target, dried in laboratory air and after drying were measured by mass spectrometry in the same manner. The spectra obtained in this manner (FIG. 17) were calibrated with the aid of singly and doubly charged ions of the molecule used for spiking. The molecular masses determined for the active hedgehog species present in solution A are summarized in the following Table 1.

TABLE 1

| Spectrum of FIG. 1/signal | Molecular mass of the active hedgehog molecule | Difference from the molecular mass of the unmodified hedgehog molecule (19560.0D) |
|---|---|---|
| A/MH$^+$ | 19795.6 D | 235.6 D |
| A/MH$^{++}$ | 19797.6 D | 237.6 D |
| B/MH$^+$ | 19796.3 D | 236.3 D |
| B/MH$^{++}$ | 19797.2 D | 237.2 D |

Taking into consideration the inaccuracy of the mass determination of ±0.01%, the difference between the molecular mass determined for the active hedgehog molecule and the molecular mass of the unmodified hedgehog molecule is 236.7±2 D. Among the known naturally occurring covalent protein modifications only esterification with C16 fatty acids (palimitic acid: mass increase by 238.4 D, monounsaturated palmitic acids: mass increase by 236.4 D) leads to an increase of the molecular mass which is compatible with the found increase in mass (Turner and Smith, molecular Biotechnol. 8 (1997) 233–249).

(4) Purification by Anion Exchange Chromatography on Poros®-Q:

In addition or alternatively to purification by means of cation exchange chromatography on Poros®-HS/M, it is also possible to purify the HA or the heparin HiTrap eluates by means of anion exchange chromatography on Poros®-Q. For this the active fractions were pooled, dialysed against 20 mM Tris/HCl, 0.05% Tween®80, pH 9.0 (=buffer D) and applied to a Poros®-Q column which had been equilibrated in buffer D. It was eluted by a gradient of 60 column volumes of 0–1000 mM NaCl in buffer D. Active fractions were identified by stimulation of alkaline phosphatase in C3H10T1/2 cells. Active hh protein eluted at a salt content of 90–175 mM NaCl. These active fractions can be further purified and characterized by means of Poros®-HS/M or RP-HPLC or SDS-PAGE and Western blot as described above.

EXAMPLE 4

Stability of the Active hh Derivative Towards Reducing Agents (1) Stability Towards Dithiothreitol (DTT)

The step eluate of a heparin-Sepharose column containing buffer A which additonally contained 1.2 M NaCl (see example 3) was diluted with 1 volume 0.05% Tween®80 and 1/10 vol. 1 M Tris/HCl, pH 8 was added for the samples at pH 8. DTT was added to the samples at final concentrations of 0 mM, 1 mM, 10 mM and 50 mM. After 2 h incubation at 37° C., each of the samples was admixed with 1/10 volumes (50 µl) 10 mg/ml BSA and dialysed against PBS. Before use in the C3H10T1/2 cell test, a final concentration of 0.1 mg/ml suramin was added to each sample in order to stabilize the remaining activity.

It turned out that the activity at pH 7.2 is stable up to a concentration of 10 mM DTT, however, at pH 8 treatment with 1 mM DTT already leads to a considerable reduction of activity. Such a pH dependency would be expected for the reduction of sulphur in disulfide bridges as well as of thioesters of fatty acids (Issartel et al., Nature 351 (1991) 759–761).

(2) Stability Towards Hydroxylamine (HA):

The step eluate of a heparin-Sepharose column with buffer A which additionally contained 1.2 M NaCl (see example 3) was adjusted with NaOH to pH 8.0 or with HCl to pH 5.5. Aliquots of these samples were each admixed with 0 mM, 66 mM, 250 mM or 1 M of $NH_2OH$ with the corresponding pH value and incubated for 14 h at RT. The samples were subsequently dialysed against 20 mM NaP, 250 mM NaCl, 0.05% Tween80, pH 7.4 and admixed with 1 mg/ml (final concentration) BSA and 0.1 mg/ml (final concentration) suramin before analysis in the cell test.

It turned out that the activity at pH 5.5 is stable up to 66 mM HA but treatment with 66 mM HA at pH 8 already led to a considerable reduction of activity. Such a pH dependency would be expected for the cleavage of thioesters but not for hydroxyl esters of fatty acids (Issartel et al., Nature 351 (1991) 759–761; Maggee et al., EMBO J. 4 (1985) 1137–1144).

EXAMPLE 5

Induction of Alkaline Phosphatase in the Cell Test (Determination of the Activity of Alkaline Phosphatase)

5000 cells of the murine mesenchymal pluripotent line C3H10T1/2 (ATCC CCl-226) were sown in each well of a 96-well microtitre plate. The cells were in 100 µl DMEM, 2 mM glutamine, 100 IU/ml penicillin, 100 µg/ml streptomycin and 10% foetal calf-serum, FCS. On the next day the active substances to be examined were added at the appropriate concentrations in a volume of 100 µl after 20–500-fold predilution in culture medium. The test was stopped after 5 days. For this purpose the supernatants were discarded and the cells were washed once with PBS. The cells were lysed in 50 µl 0.1% Triton®X-100 and frozen at −20°C. After thawing 25 µl was used for the protein determination and 25 µl for the determination of the activity of alkaline phosphatase.

Protein Determination According to the Instructions of the Manufacturer Pierce:

75 µl distilled $H_2O$ was added to the mixture, then 100 µl BCA protein reagent was added (Pierce Micro BCA, No. 23225). After 60 min the optical density (OD) at 550 nm was measured.

Activity of the Alkaline Phosphatase According to the Instructions of the Manufacturer Sigma:

100 µl reaction buffer (Sigma 221) was added to the preparation. A substrate capsule (Sigma 104-40) was dissolved in 10 ml redistilled $H_2O$ and then 100 µl was added to the test mixture by pipette. The OD was measured at 405 nm after the yellow coloration. In the reaction alkaline phosphatase converts p-nitrophenyl phosphate into p-nitrophenol.

The ODs were each converted into nmol or µg by means of standard curves. The evaluation was according to the formula:

nmol PNP per (measured) minute per mg (cell) protein

EXAMPLE 6

Comparison of the Specific Activities of Unmodified hShh From *E. coli* With the hShh Derivative Purified From BVCM In order to compare the specific activities of the diverse hh forms, hh protein was used at a defined concentration in the C3H10T1/2 cell test. In this case the protein determination was carried out for the unmodified hh protein from *E. coli* by means of its UV absorbance at 280 nm (Mach, H., et al., Anal. Biochem. 200 (1992) 74–80). The concentration of the hh derivative purified from the baculovirus fermentation supernatant was determined by means of RP-HPLC. The concentration in the stock solution was determined by integrating the area under the absorbance curve of the hh peak in the RP-HPLC where the detection was carried out at 220 and 280 nm and a calibration curve was established by an analogous chromatography using stock solutions of unmodified shh of known concentration. The relative activity of the isolated shh proteins was determined in the C3H10T1/2 cell test by determining the stimulation of the expression of alkaline phosphatase in these cells (example 5; cell test) compared to the baculovirus fermentation supernatant (BVCM after 24 hour fermentation) in a 1:40 dilution where the individual values were corrected for the base line activity of the cells in the absence of added shh. This determination of the relative activity is preferred since the stimulatability of the cells is influenced by the medium used and the preculture of the cells.

Table 2 shows the relative activities of purified, unmodified shh from *E. coli* and of the shh derivative purified from the supernatant of the baculovirus fermentation supernatant, which had been purified by chromatography on heparin-Sepharose, hydroxylapatite and Poros HS/M.

As shown in Table 2, hh protein purified from *E. coli* must be present at a concentration of ca. 240 µg/ml but the hh protein derivative only needs to be present at a concentration of ca. 2.3 ng/ml in the cell test in order to reach the same alkaline phosphatase activity as the BVCM at a 1:40 dilu tion. Thus the hh protein derivative has a ca. $10^4$–$10^5$-fold higher specific activity than the unmodified hh protein.

TABLE 2

| Hh source | Hh concentration of the stock solution | Dilution in the cell test | Hh concentration in the cell test | relative AP inducing activity |
|---|---|---|---|---|
| BVCM | 12 μg/ml | 1:40 | 0.3 μg/ml | 1 |
| Poros HS/M purified hShh derivative | 0.56 μg/ml | 1:100 | 5.6 ng/ml | 2.4 |
| Unmodified hShh monomer from *E. coli* | 860 μg/ml | 1:20 | 43 μg/ml | 0.18 |
| Buffer control | — | 1:40 | — | 0 |

EXAMPLE 7 in vivo Activity of Palmitoylated hh

The in vivo activity of modified and unmodified shh protein was examined in an animal model established for bone growth factors (Mackie & Trechsel, Bone 11 (1990) 296; Kling, L., et al., J. Bone Min. Res. 11 (Suppl. 1) (1996) 153). Seven week old female BALB/c mice were subcutaneously injected daily over a period of 15 days with 1, 10 or 50 μg shh in a volume of 50 μl into the cranial calotte. 14 days after completion of the treatment, the calottes were removed and purified of surrounding connective tissue. Subsequently the weights of the standardized explants and the X-ray density were analysed. Modified shh exhibited a higher osteoanabolic effect than unmodified shh.

EXAMPLE 8

Influence of Trypsin and Chymotrypsin on the Activity of shh

Figure 11A:
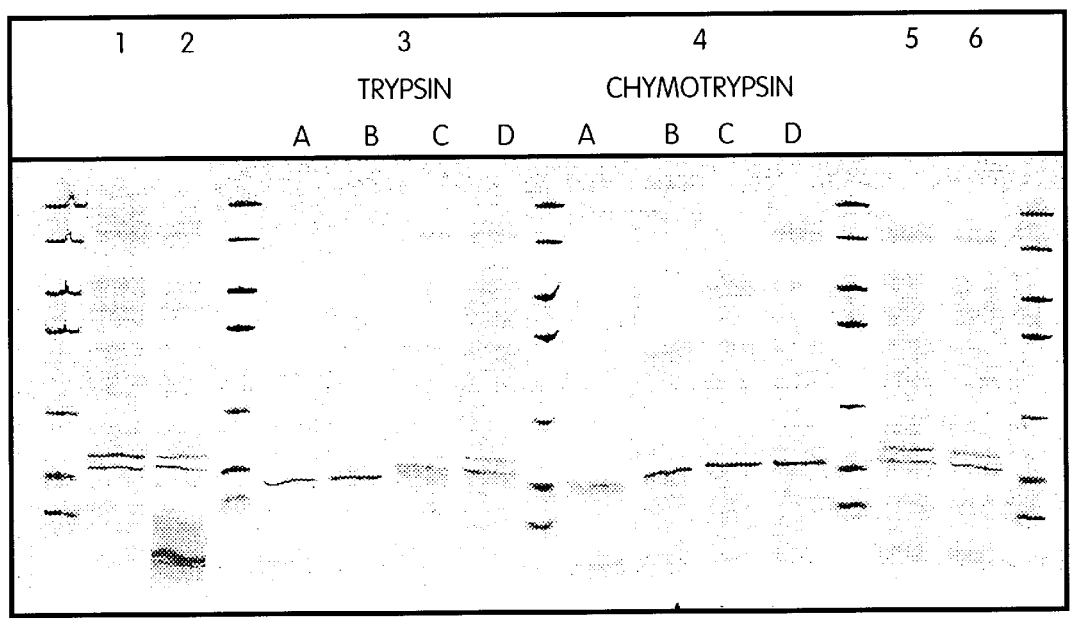
FIG. 11 shows the influence of trypsin and chymotrypsin on the activity of the hh derivative: AP active fractions after a step elution of heparin-Sepharose were adjusted to a protein concentration of 0.46 mg/ml in 10 mM Na phosphate, 0.05% Tween®80 and admixed with trypsin or chymotrypsin at a protease/protein ratio (w/w) of 1:100 (A), 1:500 (B), 1:2500 (C) and 1:10000 (D). The samples were incubated for 11 h at RT. The digestion was stopped by adding aprotinin in a 5-fold weight excess and the samples were analysed in SDS-PAGE (A:) and in the C3H10T1/2 test (B:). 1, test mixture; 2, control without protease; 3, samples treated with trypsin; 4, samples treated with chymotrypsin; 5, control trypsin (1:100) and aprotinin at t=0; 6, control chymotrypsin (1:100) and aprotinin at t=0.
Figure 11B:
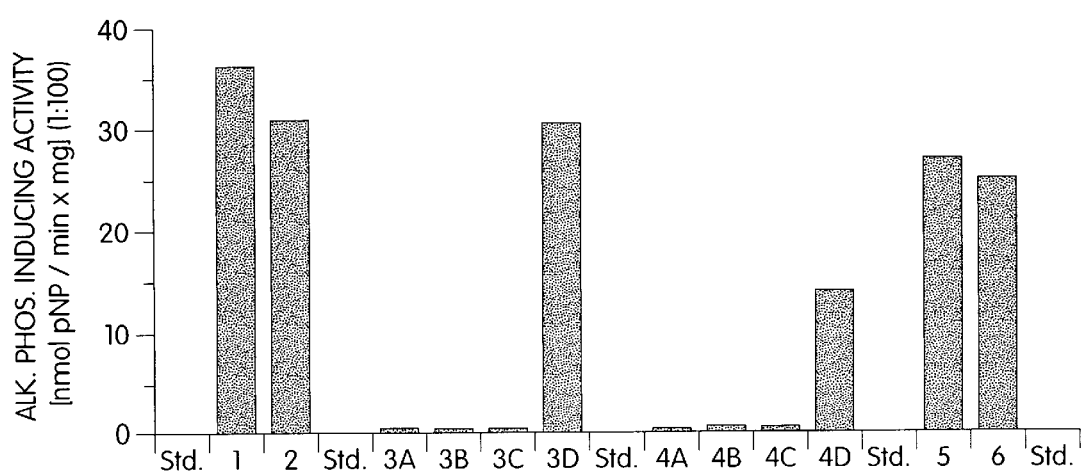
Figure 12:
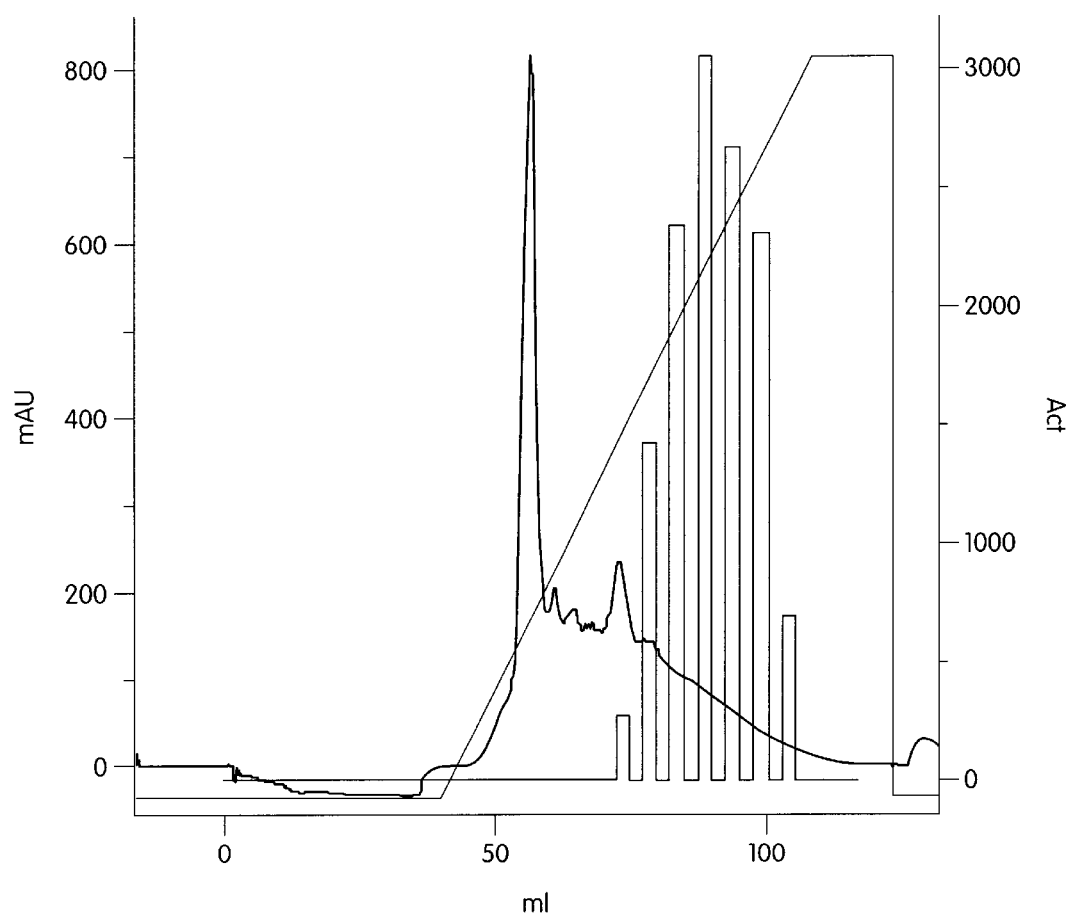
FIG. 12 is an elution diagram of the purification of dialysed active fractions of the hydroxylapatite column with a 1.7 ml Poros HS/M column. The UV-detected elution diagram is shown as a line and the activities of the fractions in the cell test are shown as bars.
Figure 13A:
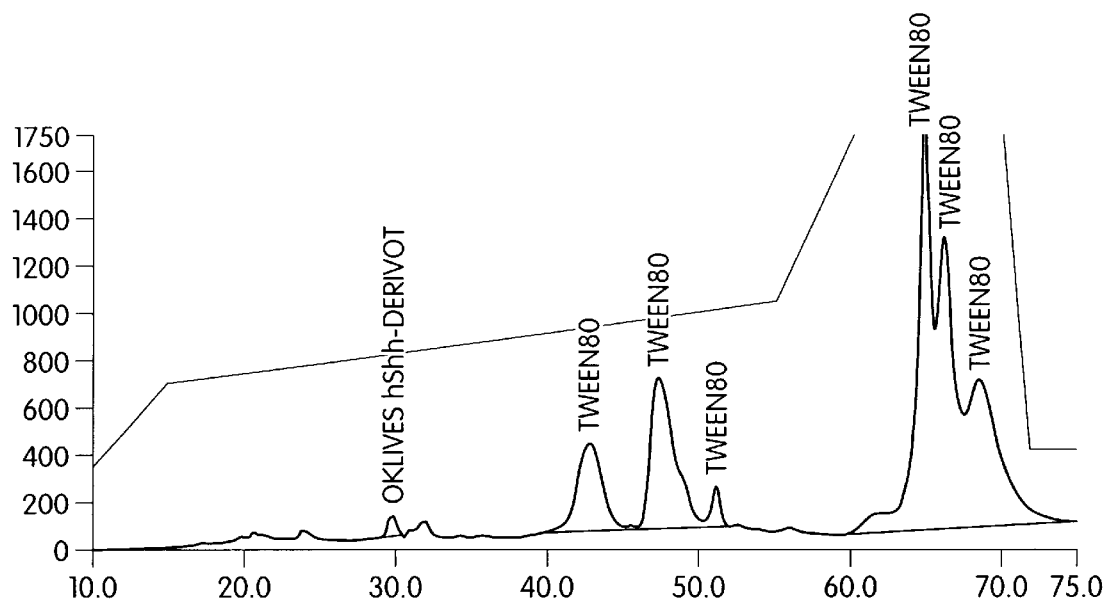
FIGS. 13A and 13B are elution diagrams of the separation of the active fractions of the Poros HS/M column by means of RP-HPLC. A: Elution diagram of 10 to 75 min. detected at 220 nm. B: Elution diagram of 15 to 40 min. detected at 280 nm.
Figure 13B:
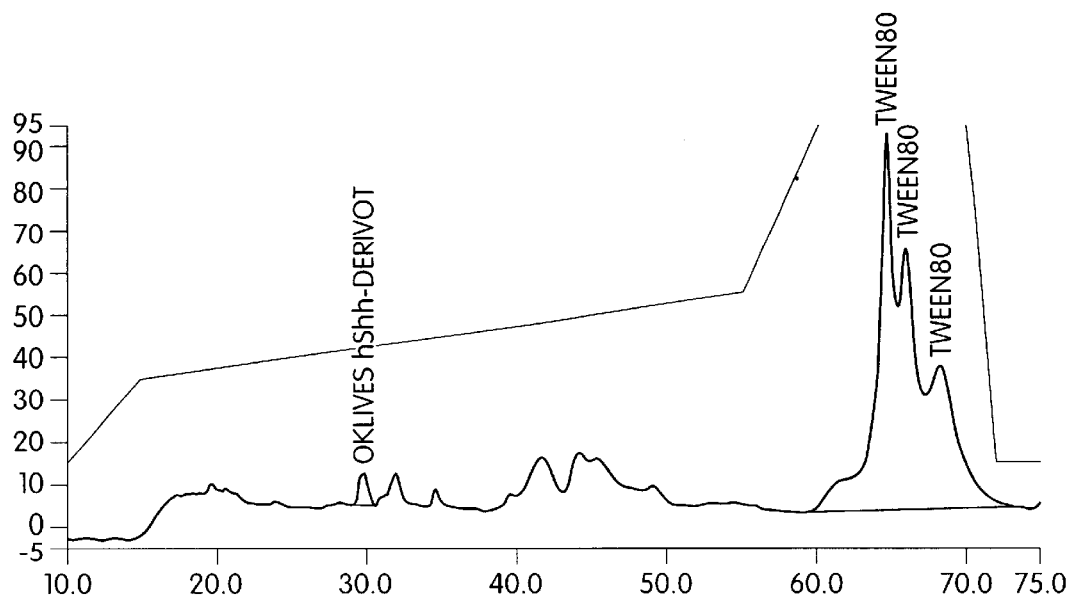
Figure 14:
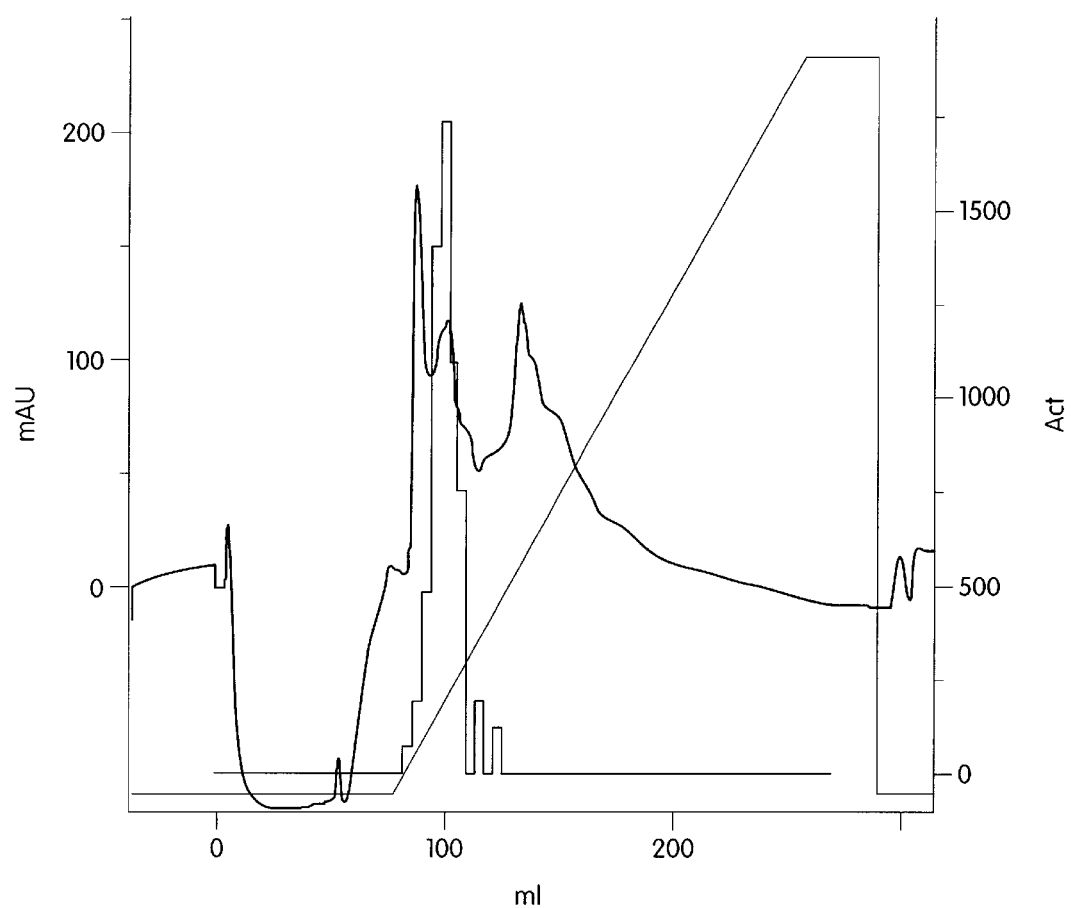
FIG. 14 is an elution diagram of the purification of the dialysed active fractions of the hydroxylapatite column with a 6 ml Poros Q column. The UV signal of the elution is shown as a line, the activity in the cell test as bars.
Figure 15:
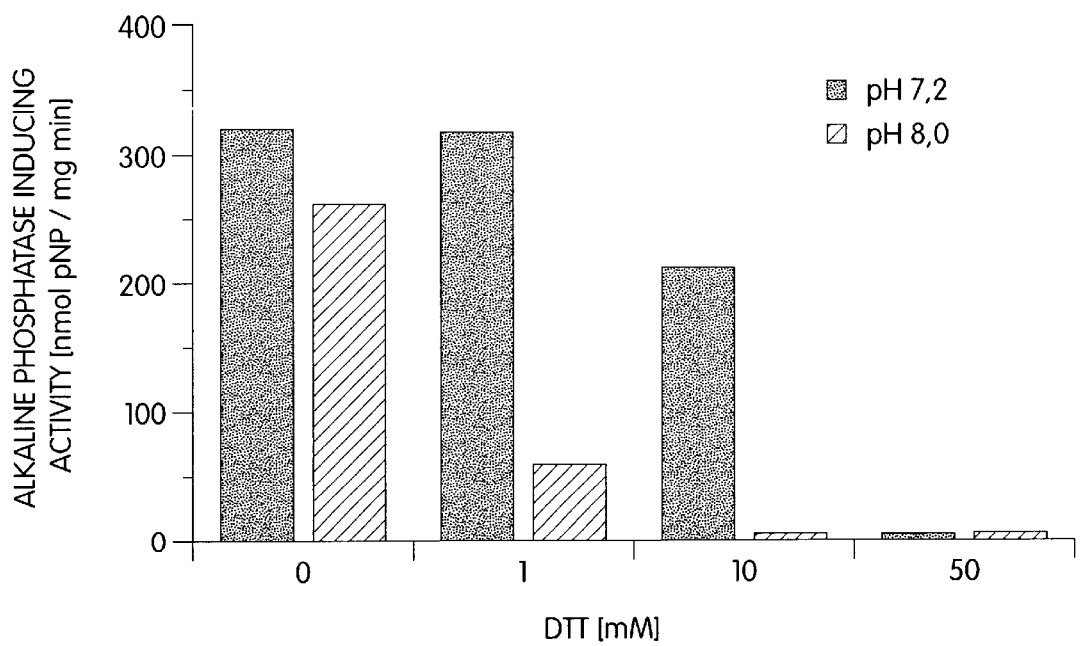
FIG. 15 shows the stability of the alkaline phosphatase inducing activity towards dithiothreitol.
Figure 16:
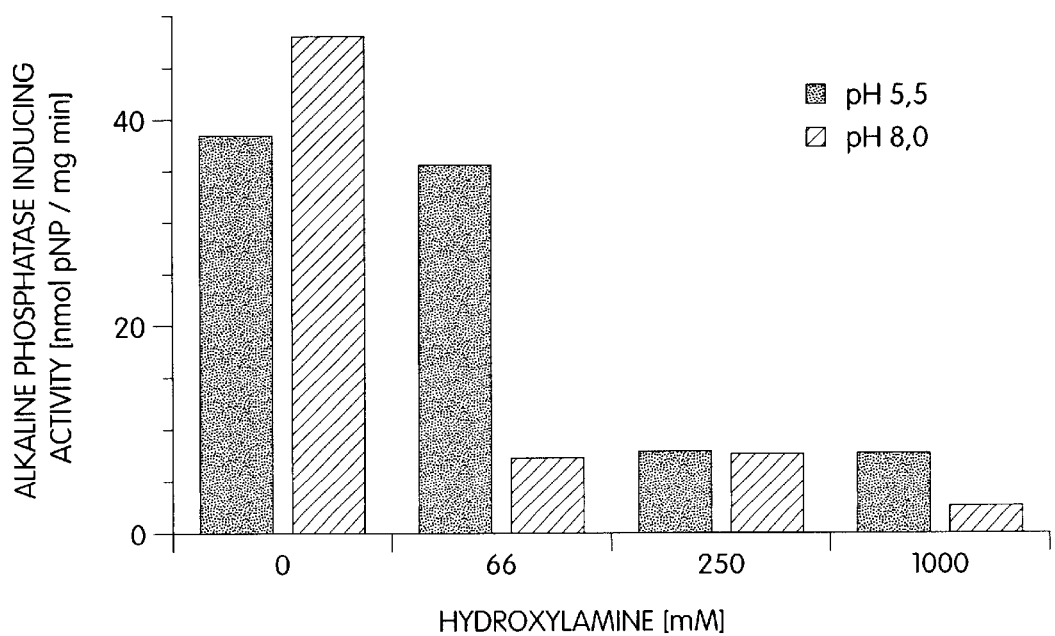
FIG. 16 shows the stability of the alkaline phosphatase inducing activity towards hydroxylamine.

After step elution of heparin-Sepharose the AP active fractions were admixed with trypsin or chymotrypsin at different protease/protein ratios. After incubation of the samples for 20 h at 25° C. the digestion was stopped by addition of aprotinin and the samples were analysed by means of SDS-PAGE and in the C3H10T1/2 test (see FIG. 11).

It turned out that the hedgehog protein is degraded to a shortened form which migrate at 20 kDa in the SDS-PAGE. By means of amino-terminal sequencing and MALDI mass spectrometry it could be shown that the mature hh protein is degraded by the chymotrypsin or trypsin treatment at a protease/protein ratio (w/w) of 1:100 to fragments in which the first 7 or 14 amino-terminal amino acids are absent. As shown by the results of the C3H10T1/2 test in FIG. 11, the alkaline phosphatase inducing activity is also reduced when the hh protein is shortened.

List of References

Asahina, J., Exp. Cell. Res. 222 (1996) 38–47
Bitgood, M. J. et al., Curr. Biol. 6 (1996) 296
Bumcrot et al., Mol. Cell. Biol. 15 (1995) 2294–2303
Cha et al., Proc. Natl. Acad. Sci. USA 94 (1997) 10577–10582
Chiang, C. et al., Nature 83 (1996) 407
Fietz, M. et al., Development (Suppl) (1994) 43–51
Hynes, M. et al., Neuron 15 (1995) 35–44
Issartel et al., Nature 351 (1991) 759–761
Karablis et al., Genes and Development 8 (1994) 277–289
Kinto et al., FEBS Letters, 404 (1997) 319–323
Kling et al., J. Bone Min. Res. 11 (Suppl. 1) (1996) 153
Lai, C. J. et al., Development 121 (1995) 2349
Mach, H., et al., Anal. Biochem. 200 (1992) 74–80
Mackie & Trechsel, Bone 11 (1990) 296
Maggee et al., EMBO J. 4 (1985) 1137–1144
Miao et al., J. Neurosci. 17 (1997) 5891–5899
Middaugh et al., Biochem 31 (1992) 9016–9024
Nakamura, T. et al., Biochem. Biophys. Res. Comm. 237 (1997) 465–469
Perrimon, N., Cell 80 (1995) 517–520
Porter, J. A. et al., Science 274 (1996) 255–259
Smith, J. C., Cell 76 (1994) 193–196
Turner and Smith, Molecular Biotechnol. 8 (1997) 233–249
U.S. Pat. No. 5,364,839
Vortkamp, A. et al., Science 273 (1996) 613
WO 97/35607
WO 93/00050
WO 95/16035
Wozney et al., Cell. Mol. Biol. of Bone, Bone Morphogenetic Proteins and their Gene Expression, 131–167, Academic Press Inc. 1993

---

What is claimed is:

1. A method for producing a hedgehog protein esterified with a fatty acid having from 14 to 20 carbon atoms comprising:

a) providing an insect cell in a medium, said medium and said insect cell being capable upon fermentation of producing a fatty acid having from 14 to 20 carbon atoms, said insect cell containing a baculovirus vector having a gene inserted therein capable of expressing a hedgehog protein;

b) fermenting said insect cell in said medium for a period of 30 hours or less to produce the fatty acid and express the hedgehog protein esterified with said fatty acid; and c) isolating said esterified hedgehog protein from the protein produced during said fermentation.

2. The method of claim 1, wherein the fermentation period of said host cell is from 24 to 27 hours.

3. The method of claim 1, further comprising isolating said esterified hedgehog protein in the presence of a protease inhibitor and a non-ionic detergent.

4. The method of claim 1, further comprising isolating said esterified hedgehog protein in the presence of suramin.

5. A process for the production of a post-translationally processed hedgehog protein comprising: expressing a gene which codes for a hedgehog protein in a baculovirus expression system in a fermentation system, purifying the cell supernatant in the presence of a protease inhibitor and a non-ionic detergent and isolating the hedgehog protein which binds to heparin-sepharose and hydroxyapatite and characterized in that this hedgehog protein:

exhibits a molecular weight of 22±2 kD as determined by SDS-PAGE under alkylating conditions, exhibits a molecular weight of 24±2 kD as determined by SDS-PAGE under reducing conditions, is stabilized with respect to its activity by suramin, is inactivated when 8 or more amino acids are cleaved N-terminally, is inactivated by 90% or more when incubated with 10 mmol/l DTE for 2.5 hours at 37° C., induces an activity for alkaline phosphatase of ca. 90 nmol pNP/min/mg at a concentration of 5 nmol/l in the presence of suramin, is not modified by cholesterol and has an at least 50-fold activity compared to the corresponding recombinant hedgehog protein isolated from the cytoplasm of *E. coli*, wherein said activity is measured as alkaline phosphatase induction in a C3H10T1/2 cell test, said process further comprising dialyzing said hedgehog protein against a buffer having 1–20 mmol/l sodium phosphate pH 6.5–7.5.

6. A process as claimed in claim 5, further comprising dialyzing said hedgehog protein against a buffer having 10–100 mmol/l sodium chloride.

\* \* \* \* \*